United States Patent
Worrell et al.

(10) Patent No.: US 9,149,325 B2
(45) Date of Patent: Oct. 6, 2015

(54) END EFFECTOR WITH COMPLIANT CLAMPING JAW

(71) Applicant: Ethicon Endo-Surgery, Inc., Cincinnati, OH (US)

(72) Inventors: Barry C. Worrell, Centerville, OH (US); Frederick E. Shelton, IV, Hillsboro, OH (US); Jerome R. Morgan, Cincinnati, OH (US); Michael S. Cropper, Edgewood, KY (US); Michael J. Vendely, Lebanon, OH (US); David C. Yates, West Chester, OH (US); David A. Witt, Maineville, OH (US); David K. Norvell, Monroe, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 101 days.

(21) Appl. No.: 13/749,889

(22) Filed: Jan. 25, 2013

(65) Prior Publication Data

US 2014/0214025 A1    Jul. 31, 2014

(51) Int. Cl.
A61B 18/12 (2006.01)
A61B 18/14 (2006.01)
A61B 18/00 (2006.01)

(52) U.S. Cl.
CPC ..... *A61B 18/1445* (2013.01); *A61B 2018/0063* (2013.01); *A61B 2018/1455* (2013.01); *A61B 2018/1495* (2013.01)

(58) Field of Classification Search
CPC ............. A61B 18/1445; A61B 2018/0063; A61B 2018/1445; A61B 2018/1452; A61B 2018/1495

USPC ............... 606/41, 45, 51, 52, 205–207
See application file for complete search history.

(56) References Cited

U.S. PATENT DOCUMENTS

| 2,541,246 | A | * | 2/1951 | Held | 606/205 |
|---|---|---|---|---|---|
| 5,281,220 | A | * | 1/1994 | Blake, III | 606/46 |
| 5,330,471 | A | * | 7/1994 | Eggers | 606/48 |
| 5,366,476 | A | * | 11/1994 | Noda | 606/206 |
| 5,396,900 | A | * | 3/1995 | Slater et al. | 600/564 |
| 5,665,085 | A | * | 9/1997 | Nardella | 606/41 |
| 6,358,249 | B1 | * | 3/2002 | Chen et al. | 606/45 |
| 6,425,896 | B1 | * | 7/2002 | Baltschun et al. | 606/51 |
| 6,500,176 | B1 | | 12/2002 | Truckai et al. | |
| 6,783,524 | B2 | | 8/2004 | Anderson et al. | |
| 7,112,201 | B2 | | 9/2006 | Truckai et al. | |

(Continued)

OTHER PUBLICATIONS

U.S. Appl. No. 61/410,603, filed Nov. 5, 2010.

*Primary Examiner* — Michael Peffley
*Assistant Examiner* — Daniel Fowler
(74) *Attorney, Agent, or Firm* — Frost Brown Todd LLC

(57) ABSTRACT

An apparatus for operating on tissue includes an end effector assembly, a body, and a shaft. The shaft extends from the body to the end effector assembly. The body is operable to communicate with the end effector assembly via the shaft. The end effector assembly includes a pair of pivoting jaws and a firing beam. The firing beam is operable to advance distally through slots in the jaws to close the jaws. One of the jaws comprises a plurality of segments that are movable relative to each other. The segments may be joined by living hinges, pivoting hinges, or sliding features. One of the jaws may be formed by a combination of a distally projecting tongue of the shaft and two members that are secured above and below the tongue, respectively. An end effector jaw may also include a resiliently biased electrode cartridge.

20 Claims, 24 Drawing Sheets

(56) References Cited

U.S. PATENT DOCUMENTS

| | | |
|---|---|---|
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 8,444,642 B2 * | 5/2013 | Contijoch et al. ............ 606/51 |
| 2002/0062136 A1 * | 5/2002 | Hillstead et al. ............ 606/205 |
| 2003/0229344 A1 * | 12/2003 | Dycus et al. ................ 606/51 |
| 2006/0047278 A1 * | 3/2006 | Christian et al. ............ 606/41 |
| 2007/0106295 A1 * | 5/2007 | Garrison et al. ............ 606/50 |
| 2009/0125027 A1 * | 5/2009 | Fischer .................... 606/46 |
| 2010/0089970 A1 * | 4/2010 | Smith et al. ............... 227/175.1 |
| 2010/0179540 A1 * | 7/2010 | Marczyk et al. ............ 606/41 |
| 2010/0249776 A1 * | 9/2010 | Kerr ....................... 606/51 |
| 2011/0054469 A1 * | 3/2011 | Kappus et al. .............. 606/46 |
| 2011/0071525 A1 * | 3/2011 | Dumbauld et al. ........... 606/51 |
| 2011/0087218 A1 | 4/2011 | Boudreaux et al. |
| 2011/0238065 A1 | 9/2011 | Hunt et al. |
| 2011/0251612 A1 * | 10/2011 | Faller et al. ............... 606/52 |
| 2011/0282339 A1 * | 11/2011 | Weizman et al. ............ 606/33 |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0083784 A1 * | 4/2012 | Davison et al. ............. 606/48 |
| 2012/0116379 A1 | 5/2012 | Yates et al. |
| 2013/0023868 A1 | 1/2013 | Worrell et al. |
| 2013/0030428 A1 | 1/2013 | Worrell et al. |

* cited by examiner

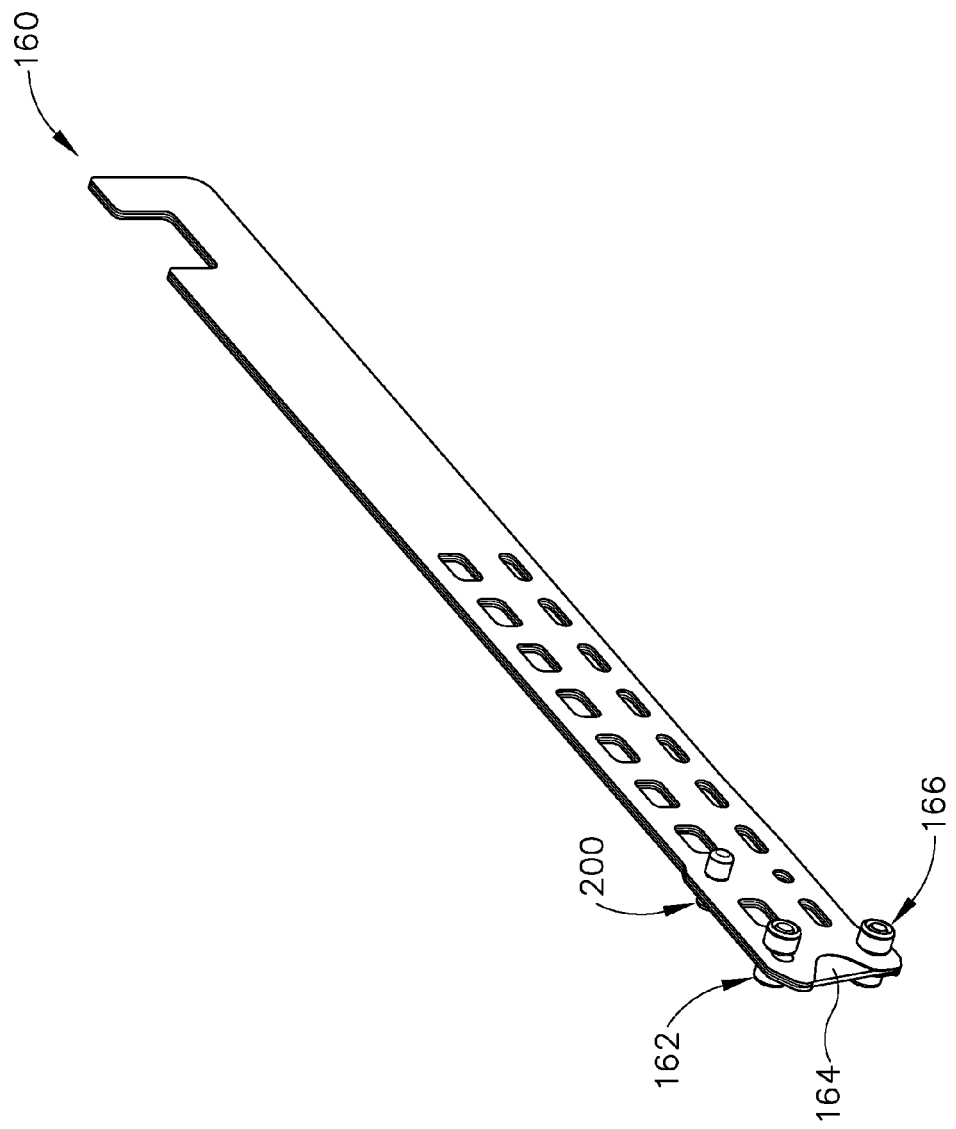

END EFFECTOR WITH COMPLIANT CLAMPING JAW

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. patent application Ser. No. 13/622,729, entitled "Surgical Instrument with Multi-Phase Trigger Bias," filed Sep. 19, 2012 and published as Pub. No. 2013/0030428 on Jan. 31, 2013, and issued as U.S. Pat. No. 9,089,327 on Jul. 28, 2015, the disclosure of which is incorporated by reference herein; and U.S. patent application Ser. No. 13/622,735, entitled "Surgical Instrument with Contained Dual Helix Actuator Assembly," filed Sep. 19, 2012 and published as Pub. No. 2013/0023868 on Jan. 24, 2013, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a perspective view of the firing beam of FIG. 5;

Figure 1:
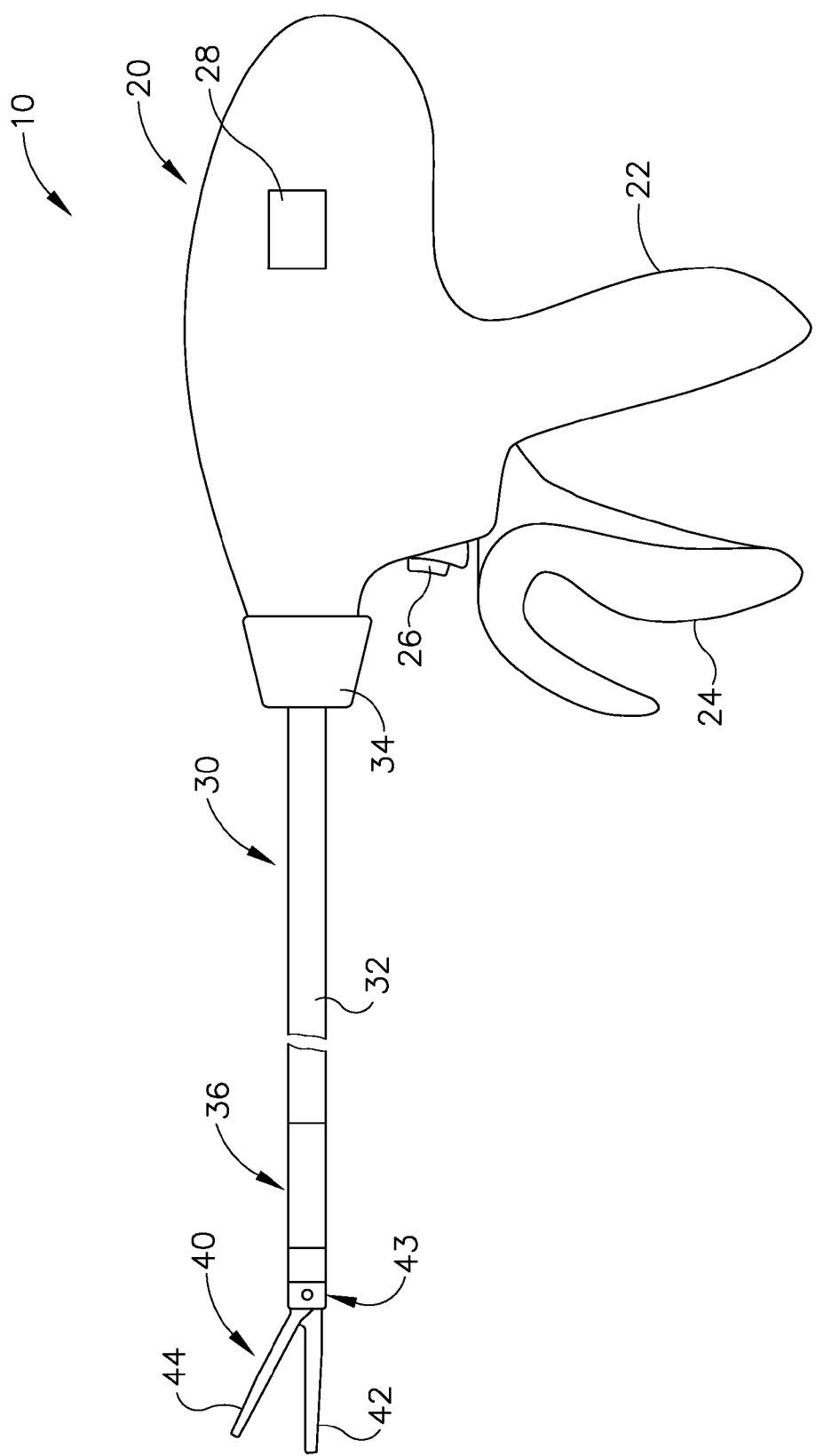
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pat. No. 8,939,974; U.S. Pub. No. 2012/0116379; U.S. Pub. No. 2012/0078243; U.S. Pub. No. 2012/0078247; U.S. Pat. No. 9,089,327 and/or U.S. patent application Ser. No. 13/622,735, published as Pub No. 2013/0023868. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes an outer sheath (32) and an articulation section (36). Articulation section (36) is operable to selectively position end effector (40) at various angles relative to the longitudinal axis defined by sheath (32). Articulation section (36) of shaft (30) may take a variety of forms. By way of example only, articulation section (36) may be configured in accordance with one or more teachings of U.S. Pub. No. 2012/0078247, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively position end effector (40) at various angles relative to the longitudinal axis defined by shaft (30). By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. patent application Ser. No. 13/622,735, published as Pub. No. 2013/0023868, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
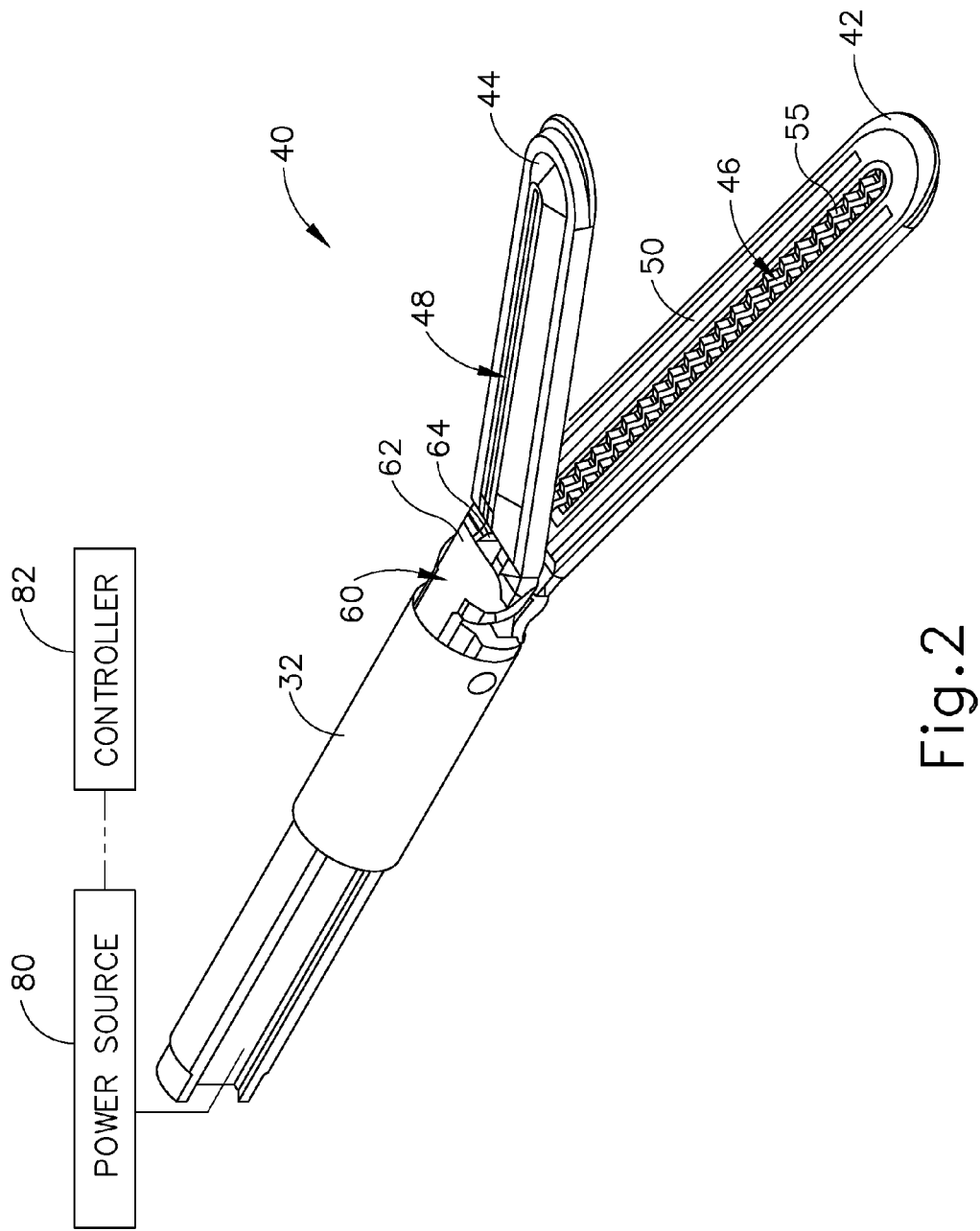
FIG. 2 depicts a perspective view of the end effector of the instrument of FIG. 1, in an open configuration.
Figure 3:
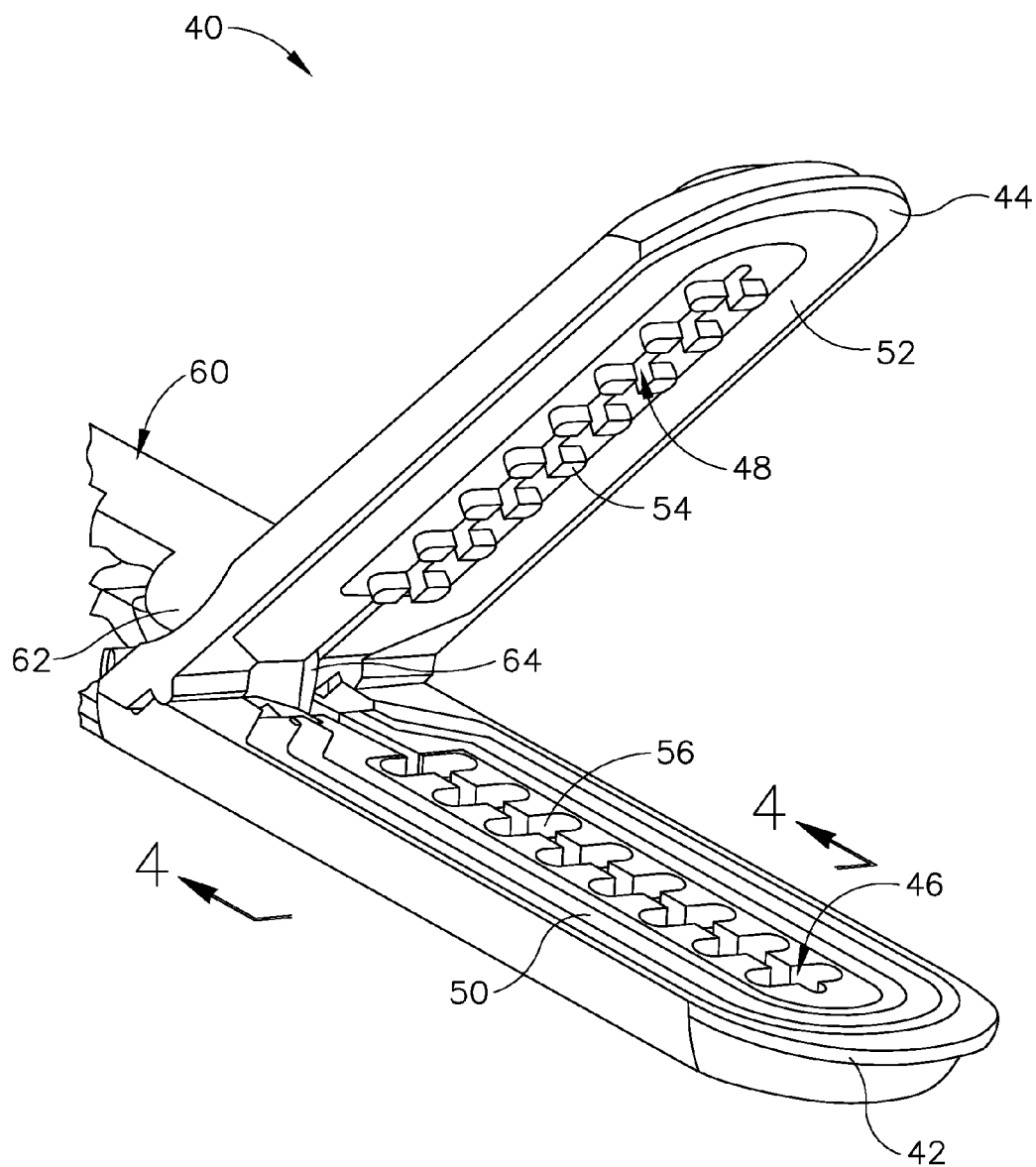
FIG. 3 depicts another perspective view of the end effector of the instrument of FIG. 1, in an open configuration.
Figure 4:
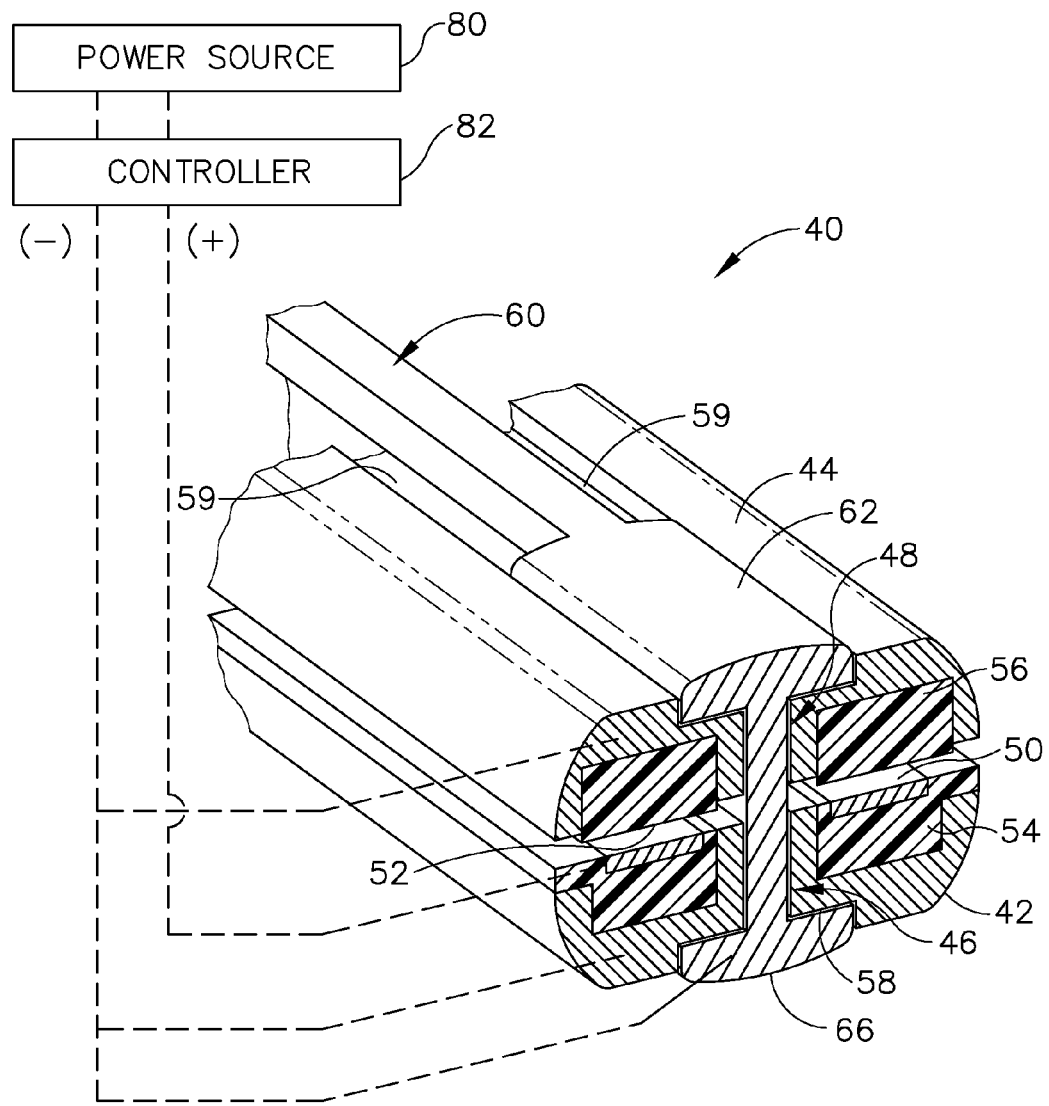
FIG. 4 depicts a cross-sectional end view of the end effector of FIG. 2, taken along line 4-4 of FIG. 3, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to)

the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary End Effector Assemblies

End effector (40) is operable to seal tissue as described above in part by applying forces on jaws (42, 44) to pivot jaw (44) toward jaw (42) and close jaws (42, 44) about tissue. Electrodes within jaws (42, 44) may be utilized to seal the clamped tissue and firing beam (60) may be advanced to sever the clamped tissue before, during, or after the tissue is sealed. Flanges (62, 66) of firing beam (60) advance through recesses (58, 59) of jaws (42, 44) as described above. In instances where relatively thick and/or dense tissue may be encountered, a surgeon may desire to increase the compressive forces applicable to end effector (40) and/or to localize the forces in succession along regions or sections of jaws (42, 44). Examples of variations to end effector (40) that may provide such an effect will be describe in greater detail below. It should be understood that these examples apply tissue clamping forces in a linearly progressing succession of localized points or regions along the jaws instead of having the clamping forces being applied along the entire length of the jaws throughout the clamping process.

Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as electrosurgical instruments. By way of example only, the below teachings may be incorporated into a linear surgical stapler (e.g., endocutter). Various other suitable devices and settings in which the below teachings may be applied will be apparent to those of ordinary skill in the art in view of the teachings herein.

A. Exemplary End Effector with Segmented Jaw with Living Hinges

Figure 5:
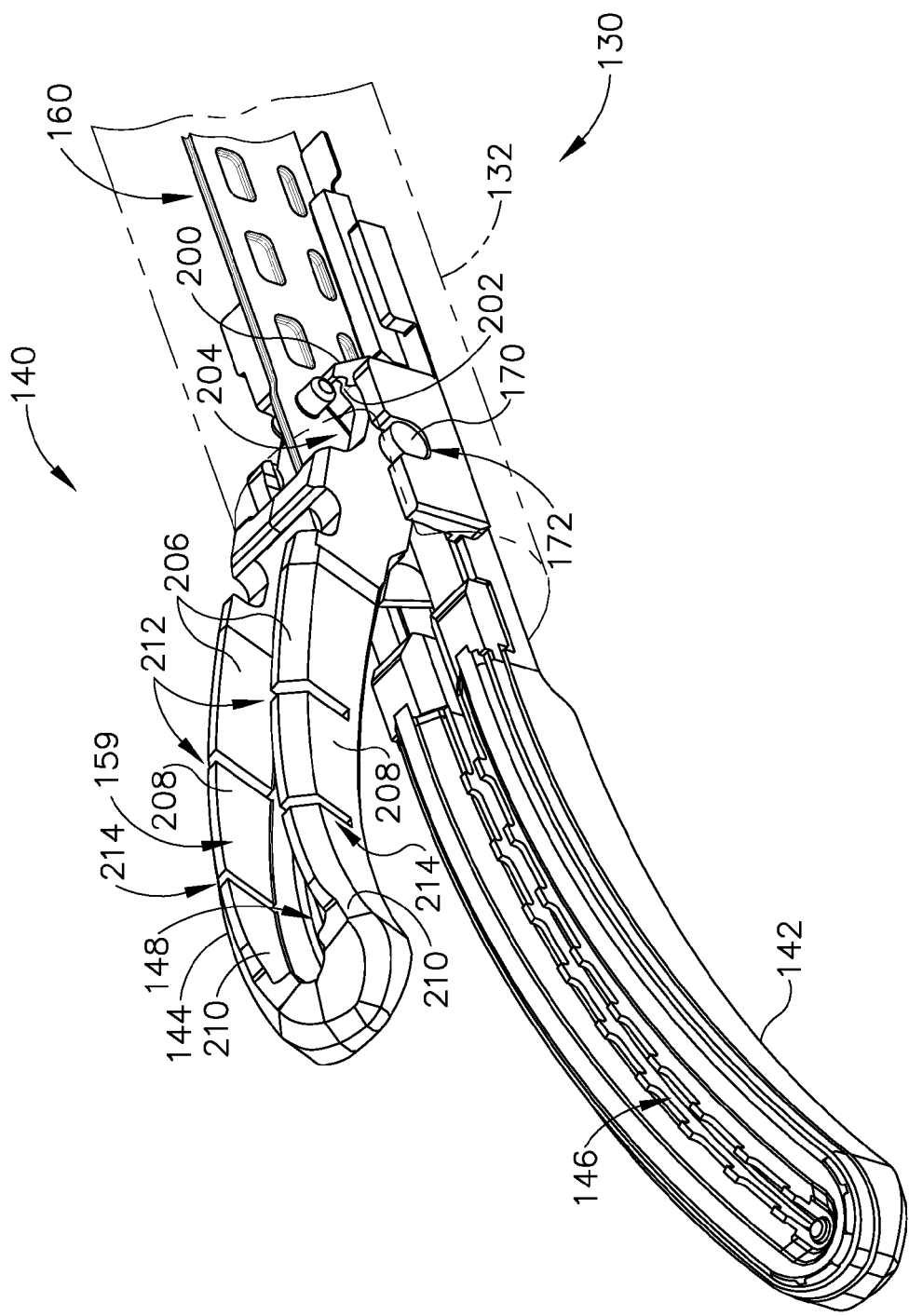
FIG. 5 depicts a perspective view of an exemplary end effector having a firing beam, a compliant and segmented upper jaw, and rigid lower jaw.

FIGS. 5-7C show an end effector (140) including a rigid lower jaw (142) and an upper jaw (144) that is segmented and compliant. It should be understood that end effector (40) may be ready substituted with end effector (140). Jaws (142, 144) include electrodes similar to those described above for jaws (42, 44). The electrode of upper jaw (144) is configured to flex with upper jaw (144), without causing damage to the electrode. Lower jaw (142) is fixed with respect to outer sheath (132) of shaft (130), which is similar to shaft (30) described above. FIG. 5 shows that lower jaw (142) has a laterally curved design such that lower jaw (142) has a first radius of curvature. Upper jaw (144) also has a laterally curved design having the first radius of curvature such that upper jaw (144) is sized and shaped to pivotally close against lower jaw (142). Of course, jaws (142, 144) need not be laterally curved; and could instead be substantially straight. Upper jaw (144) includes slot (148) and recess (159) disposed above slot (148). Lower jaw (142) includes slot (146) and recess (158), which has a similar form to recess (159), disposed below slot (146). Upper jaw (144) includes transversely extending pins (170) that are received in complementary slots (172) of lower jaw to provide a pivotal coupling between jaws (142, 144).

Firing beam (160) is similar to firing beam (60) except as described below. FIG. 6 shows firing beam (160) as including distal blade (164), jaw opening pin (200), and a pair of distal closure pins (162, 166). Distal closure pins (162, 166) are received in slots defined in firing beam (160) and include ends laterally extending from each side of the receiving slot. Distal closure pins (162, 166) close jaws (144, 142) in a manner similar to that described above with respect to flanges (62, 66) and jaws (44, 42). As firing beam (160) is received within slots (148, 146) of jaws (144, 142), distal closure pins (162, 166) are respectively receivable and advancable within recesses (159, 158) of jaws (144, 142) to urge jaw (144) toward jaw (142) by bearing against recess (159) formed in jaw (144). Jaw opening pin (200) is proximally spaced from distal closure pins (162, 166) and is configured to advance up proximal ramp surface (202) of upper jaw (144) to pivot upper jaw (144) away from lower jaw (142) and to be received in groove (204) of upper jaw (144). As distal closure pins (162, 166) advance along recesses (159, 158), jaw opening pin (200) advances along recess (159) of jaw (144).

Upper jaw (144) includes flexible segments (206, 208, 210) adjoined by living hinge sections (212, 214) that are disposed below cutouts in exterior walls of upper jaw (144). The exterior wall cutouts assist to provide clearance for a flexing backward motion of segments (208, 210) of upper jaw (144) at living hinge sections (212, 214). Upper jaw (144) and segments (206, 208, 210) may comprise a flexible material as will be apparent to those of ordinary skill in the art in view of the teachings herein. For example, upper jaw (144) may be formed at least in part using spring steel. Such a material may also provide a smooth bearing surface for distal closure pins (162, 166) of firing beam (160). The smooth bearing surface may be electroplated to further provide a smooth surface finish and an improved thickness tolerance. Other suitable materials and processes that may be used to form upper jaw (144) will be apparent to those of ordinary skill in the art in view of the teachings here. While upper jaw (144) is shown to include flexible segments (206, 208, 210), additionally or alternatively, lower jaw (142) may include similar flexible segments.

Figure 7A:
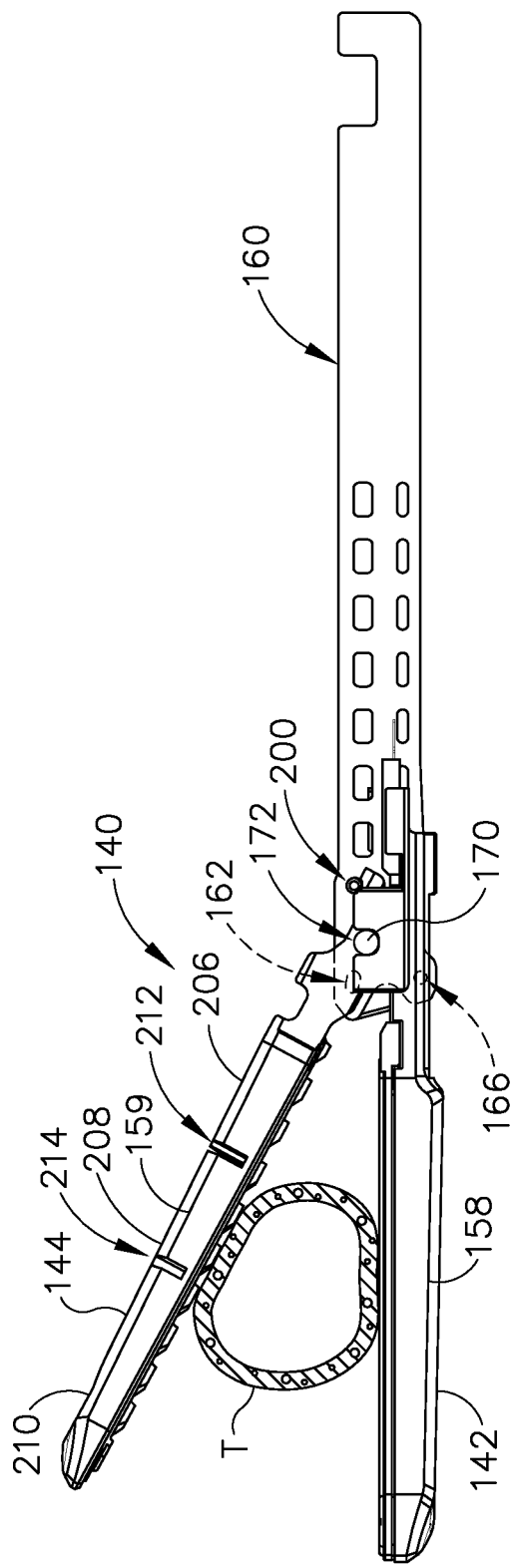
FIG. 7A depicts a side elevational view of the end effector of FIG. 5, with the firing beam in a proximal position and the upper jaw of the end effector in an open position.
Figure 7B:
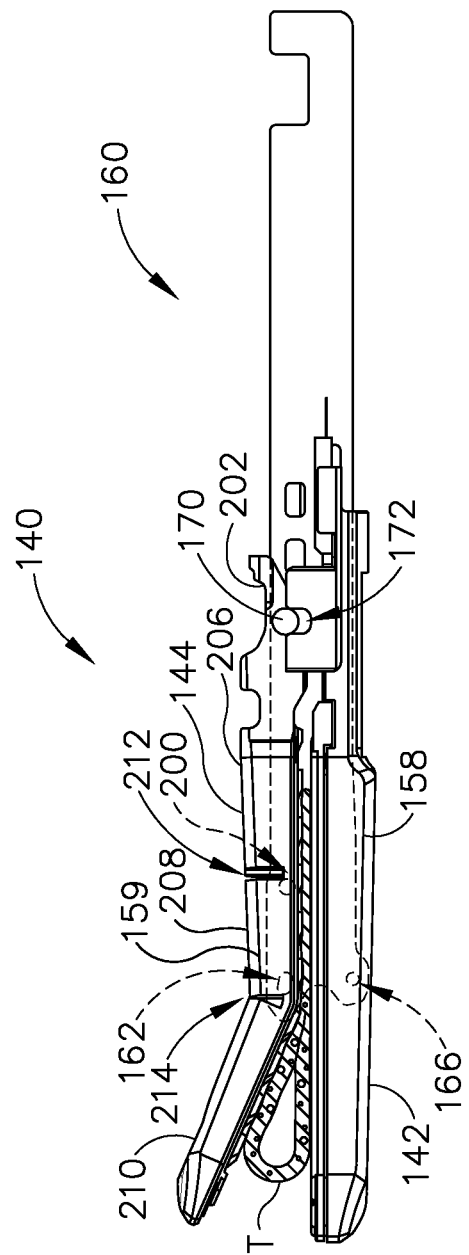
FIG. 7B depicts a side elevational view of the end effector of FIG. 5, with the firing beam in an intermediate position and the upper jaw of the end effector flexing while clamping down on tissue.
Figure 7C:
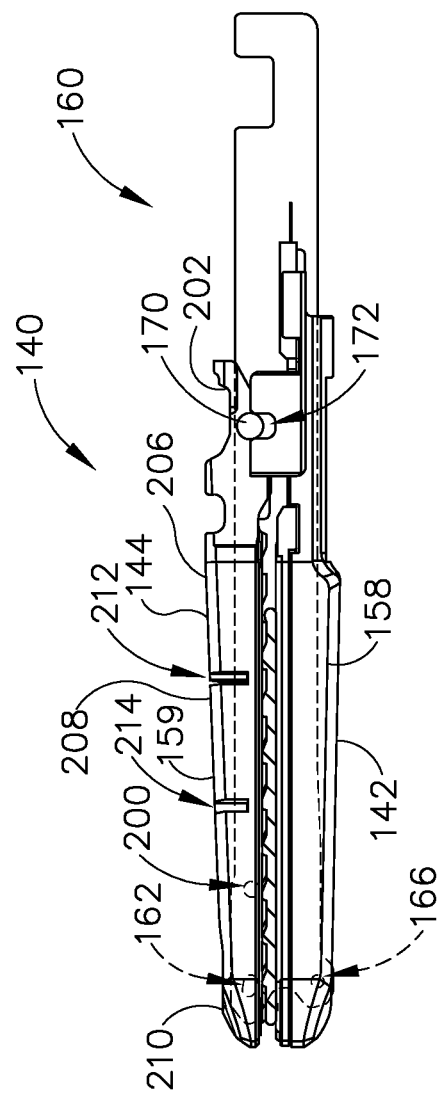
FIG. 7C depicts a side elevational view of the end effector of FIG. 5, with the firing beam in a distal position and the upper jaw of the end effector in a closed position.
Figure 8:
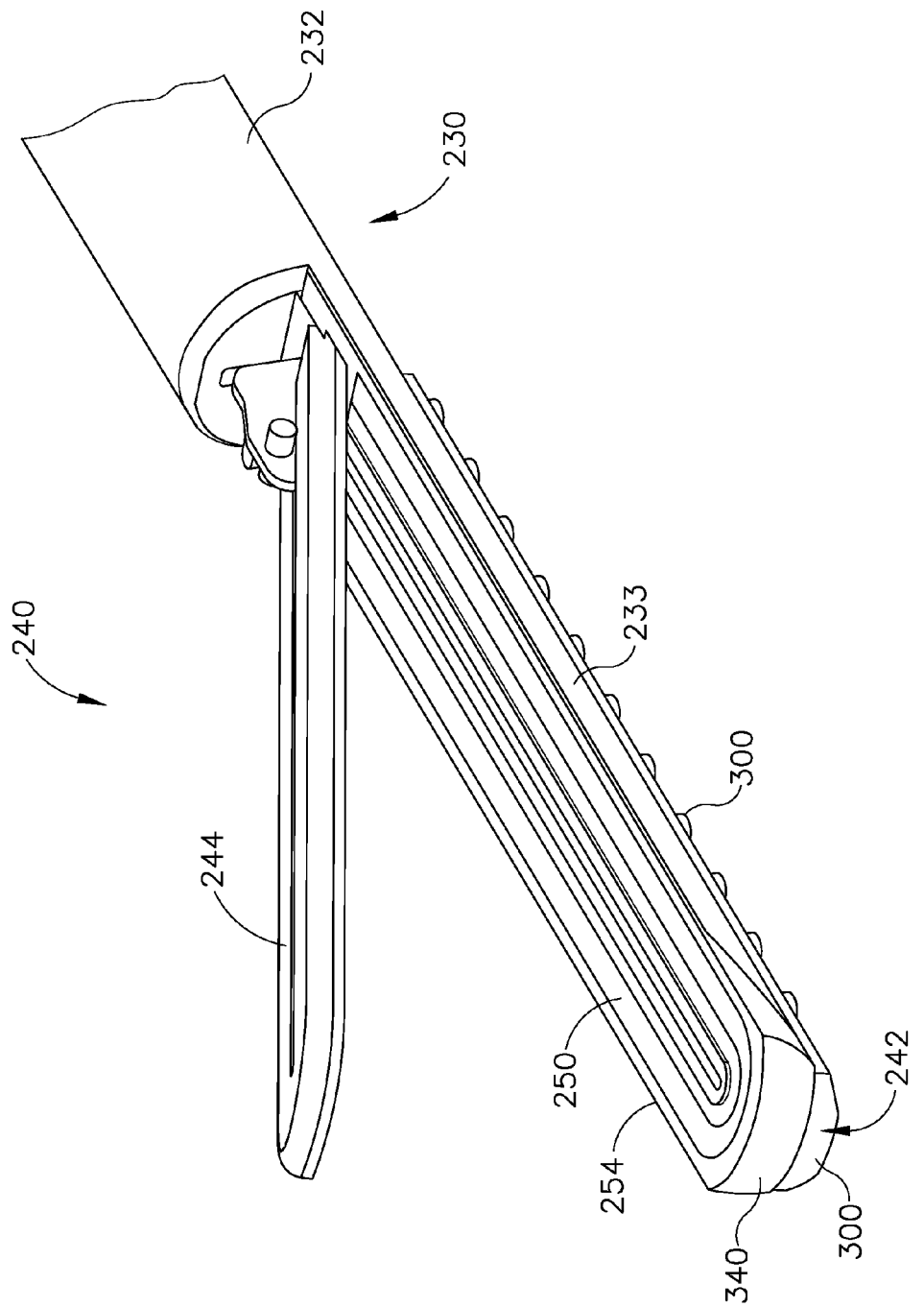
FIG. 8 depicts a perspective view of an exemplary alternative end effector having a compliant non-segmented upper jaw and a rigid lower jaw.

FIGS. 7A-7C show end effector (140) in operation in different stages in which segments (206, 208, 210) successively clamp down and close against tissue (T). In FIG. 7A, tissue T is captured between open jaws (142, 144) as firing beam (160) begins to advance. Firing beam (160) then advances to a position proximal to living hinge (212) to urge segment (206) down toward lower jaw (142). Living hinge (212) flexes to allow segments (208, 210) to deflect upwardly away from lower jaw (142), such that segments (208, 210) are angled relative to lower jaw (142) while segment (206) is substantially parallel to lower jaw (142). The closure force imposed by firing beam (160) on upper jaw (144) is substantially limited to segment (206) through this range of travel.

As firing beam (160) continues to advance distally, distal closure pins (162, 166) pass living hinge (212), and segments (206, 208) are thereby driven to positions where they are substantially parallel with lower jaw (142) as shown in FIG. 7B. Living hinge (214) flexes to allow segment (210) to deflect upwardly, such that segment (210) is angled with respect to lower jaw (142). Thus, the closure force imposed by firing beam (160) on upper jaw (144) has moved in a succession from segment (206) to segment (208) through this range of travel.

In FIG. 7C, distal closure pins (162, 166) have been distally advanced to a distal most position in which a clampable portion of tissue (T) is fully clamped between jaws (142, 144), which are fully closed with respect to each other. At this stage all segments (206, 208, 210) are substantially parallel to lower jaw (142) and tissue (T) is fully clamped and severed. Electrodes along the lengths of jaws (142, 144) of end effector may seal the edges surrounding the severed tissue in a manner as described above for end effector (40). Firing beam (160) may then be retracted proximally, with jaw opening pin (200) engaging proximal ramp surface (202) to open upper jaw (144) to release the sealed tissue. End effector (140) may then be repositioned to perform another act clamping, sealing, and cutting tissue.

B. Exemplary End Effector with Stud-Receiving Member

FIGS. 8-13B show another exemplary end effector (240) and/or components of exemplary end effector (240) that may be readily used as a substitute for end effector (40). End effector (240) includes an upper jaw (244) and a lower jaw (242), which extends from a tube (232) of a shaft (230). Shaft (230) is similar to shaft (30) described above. Upper jaw (244) is pivotally coupled to lower jaw (242) by pivoting jaw closure member (312), which will be described in greater detail below. Pivoting jaw closure member (312) is operable to pivot upper jaw (244) to an open position with respect to lower jaw (242). Upper jaw (244) is pivotally closeable against lower jaw (242) to clamp tissue for cutting and sealing.

Figure 9:
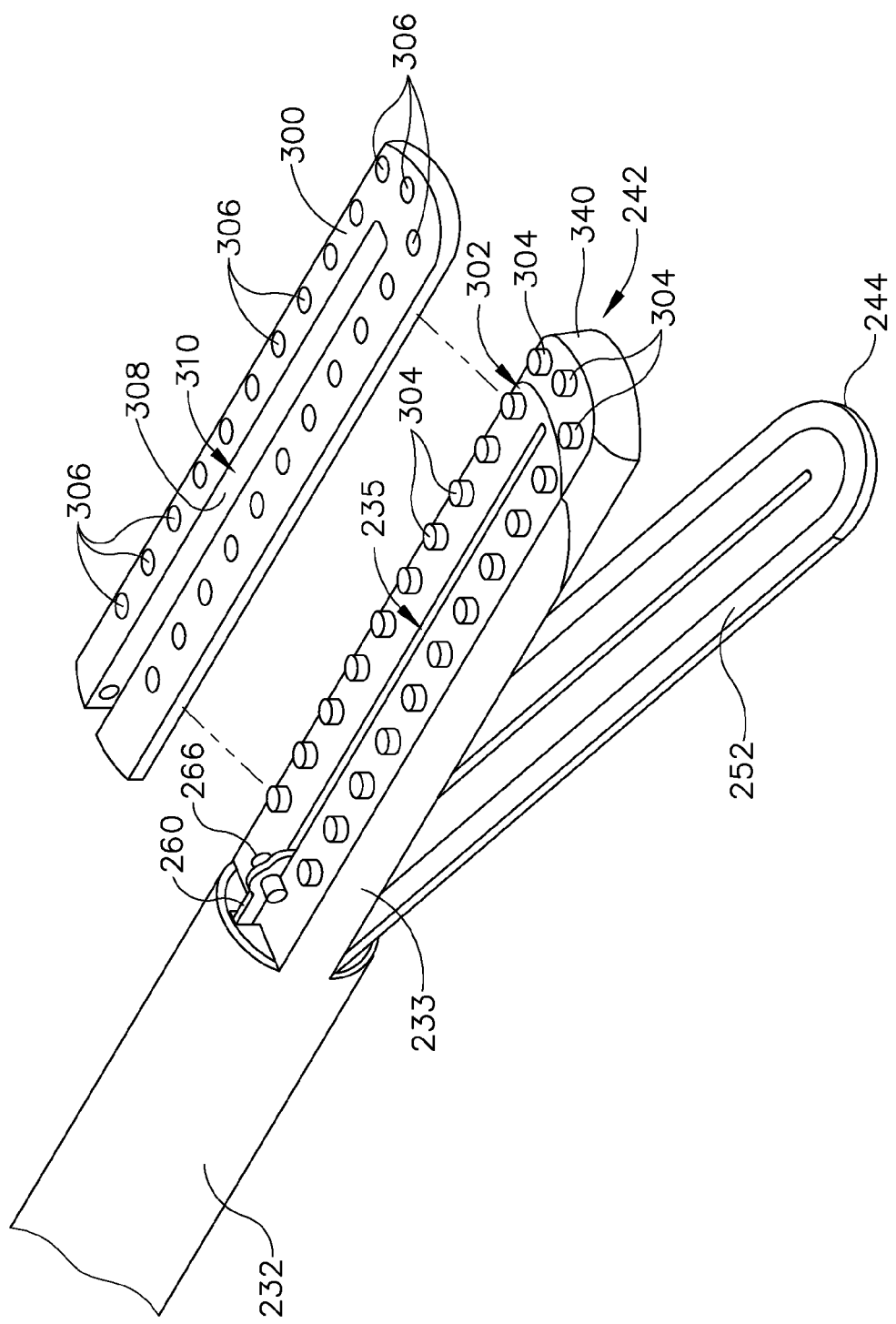
FIG. 9 depicts an exploded bottom perspective view of the end effector of FIG. 8 in which a stud-receiving member is removed from the lower jaw.
Figure 10:
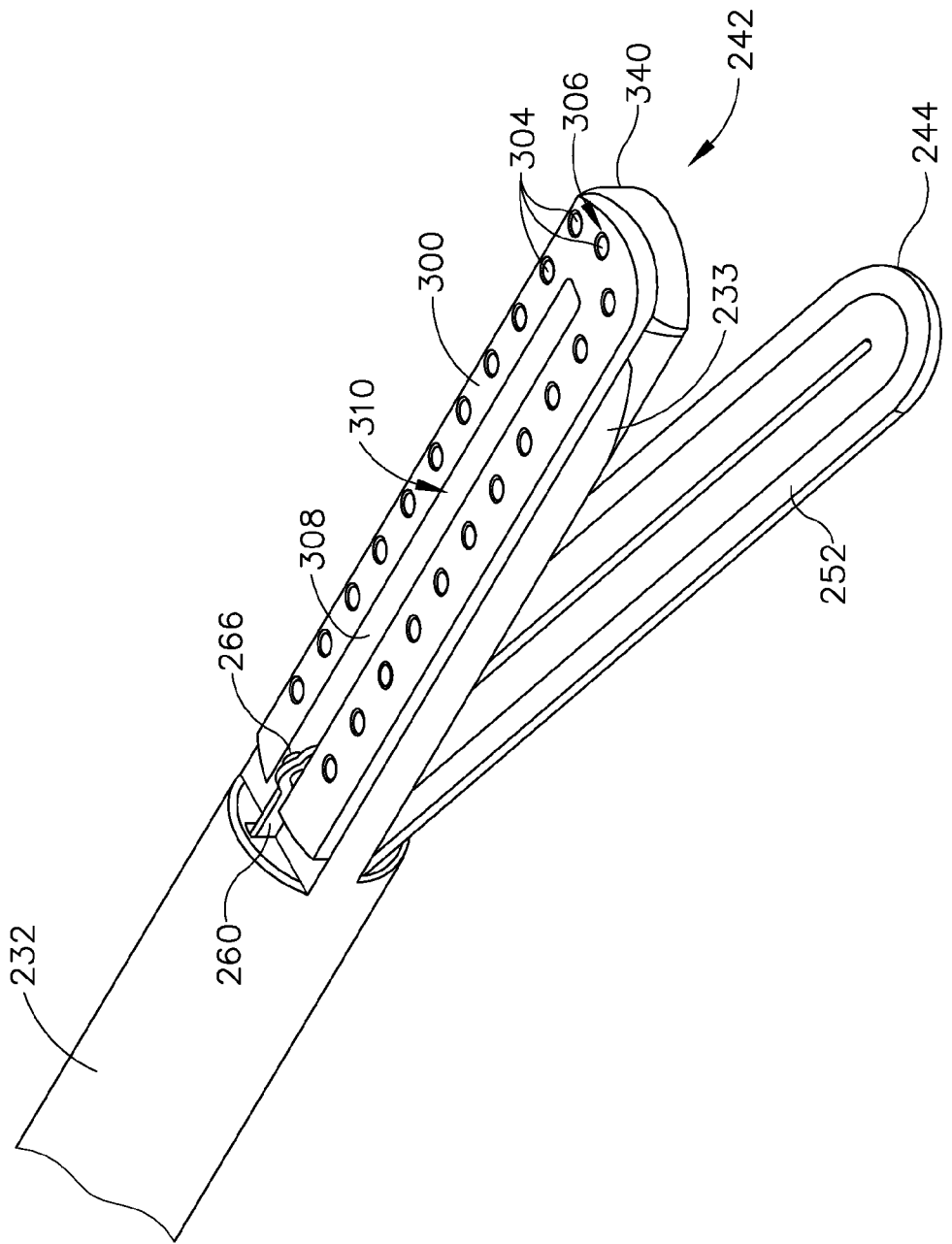
FIG. 10 depicts a perspective bottom view of the end effector of FIG. 8 in which the stud-receiving member is welded to the lower jaw.
Figure 11:
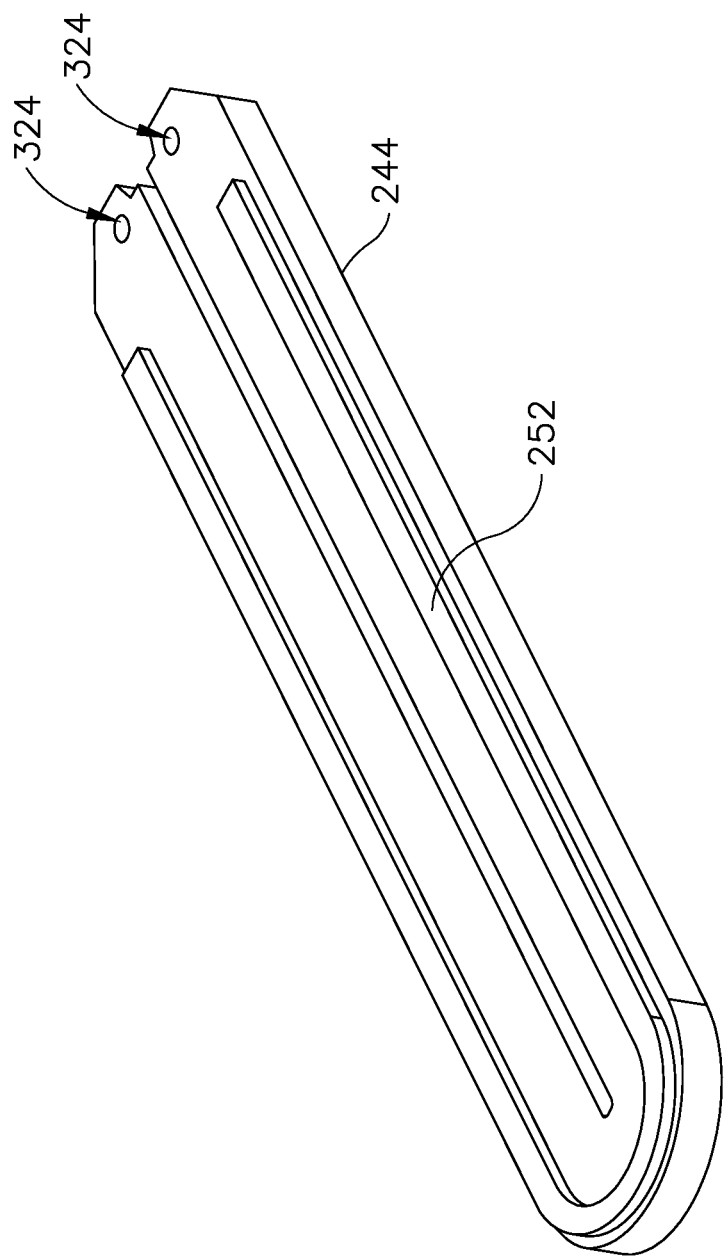
FIG. 11 depicts a perspective bottom view of the upper jaw of the end effector of FIG. 8.

FIGS. 9-11 show upper jaw (244) with electrode surface (252) disposed on an underside of upper jaw (244). Upper jaw (244) is stamped from a high strength stainless steel in the present example, though it should be understood that any other materials and/or processes may be used as will be apparent to those of ordinary skill in the art in view of the teachings herein. The electrode is mechanically attached to and insulated from upper jaw (244). The electrode may be insulated from the rest of upper jaw (244) by an insulative, non-conducting coating comprising ceramic, plastic, or any other suitable material as will be apparent to those of ordinary skill in the art in view of the teachings herein. In some versions, upper jaw (244) is able to deform as upper jaw (244) clamps on tissue. For instance, upper jaw (244) may be resiliently biased to assume a straight configuration; yet may also deform in response to lateral stresses imposed by tissue that is being clamped between jaws (242, 244). By way of example only, upper jaw (244) and/or lower jaw (244) may be comprised of materials and act in a manner as described for the jaws of U.S. Patent App. Publ. No. 2011/0238065, entitled "Surgical Cutting and Sealing Instrument with Reduced Firing Force," published Sep. 29, 2011 and issued as U.S. Pat. No. 8,696,665 on Apr. 15, 2014, the disclosure of which is incorporated by reference herein.

Figure 14:
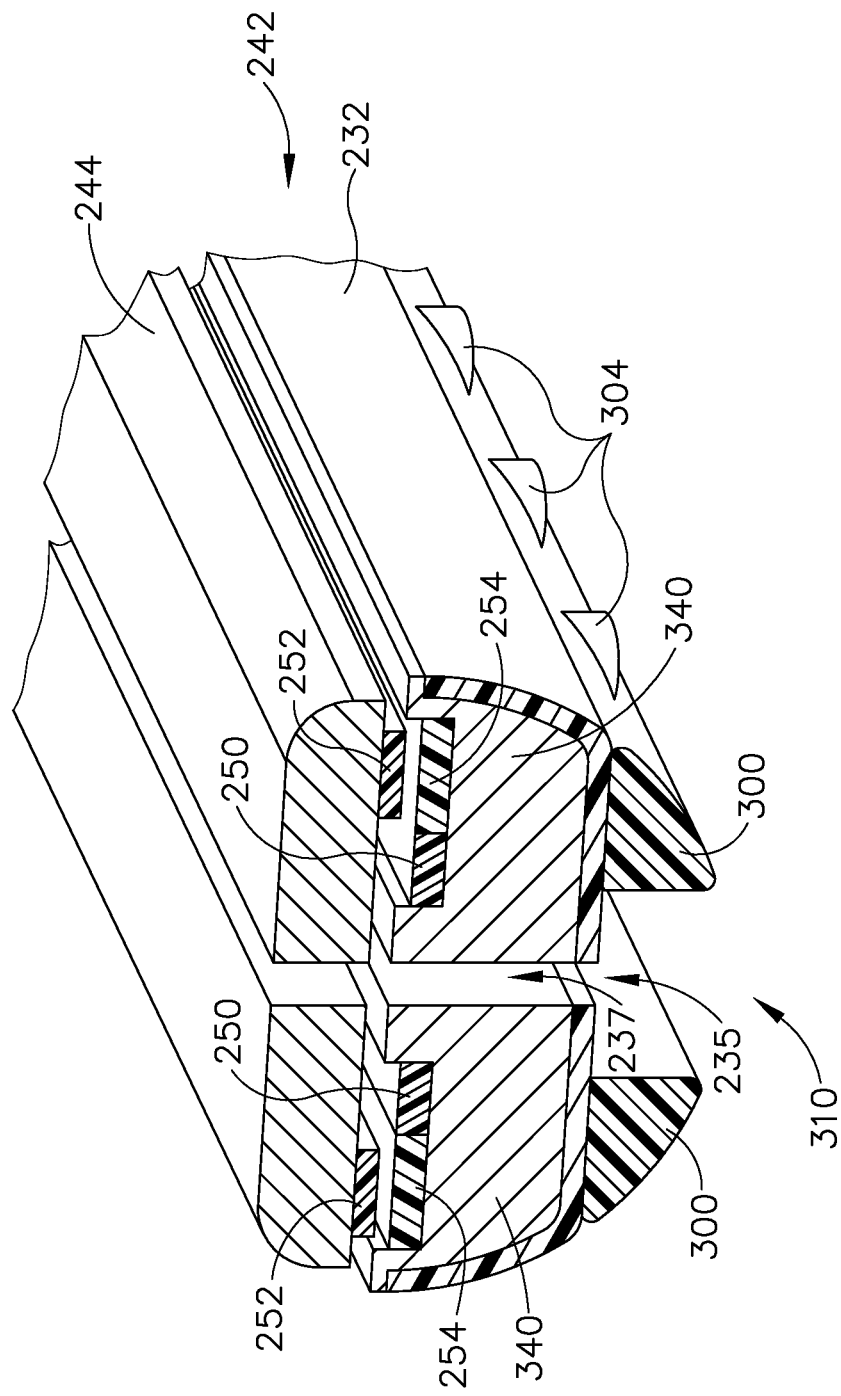
FIG. 14 depicts a cross-sectional perspective view of the end effector of FIG. 8 in a closed position.

As best seen in FIGS. 9-10 and 14, lower jaw (242) is formed by an assembly including insulator body (340), stud-receiving member (300), and tongue (233) of tube (232). In the present example, these components are joined together in a heat staking process, though it should be understood that any other suitable processes may be used. Insulator body (340) includes studs (304) that extend from an undersurface of insulator body (340). Tongue (233) includes apertures (302) sized and shaped to receive studs (304). Stud-receiving member (300) also includes apertures (306) sized and shaped to receive studs (304). Stud-receiving member (300) assists to strengthen the assembly forming lower jaw (242) to allow more force to be loaded onto lower jaw (242) when tissue is clamped between jaws (242, 244).

During assembly of lower jaw (242), studs (304) are inserted through apertures (302) of tongue (233) and through apertures (306) of stud-receiving member (300), with tongue (233) being interposed between insulator body (340) and stud-receiving member (300). Insulator body (340) is then heat-staked to stud-receiving member (300) with tongue (233) disposed between insulator body (340) and stud-receiving member (300), such that the three components form a unitary assembly. In particular, studs (304) are heated to deform and secure to stud-receiving member (300), thereby securing stud-receiving member (300), insulator body (340), and tongue (233) together. Of course, any other suitable assembly techniques may be used.

Inner surfaces (308) of stud-receiving member (300) define a slot (310) that is positioned to correspond with a slot (237) defined by insulator body (340) and a slot (235) defined by tongue (233). Slot (308) is sized and shaped to slidingly receive a pin (266) of a firing beam (260). Slots (235, 237) are narrower than slot (310), and are configured to slidingly receive firing beam (260).

As best seen in FIG. 14, an upper surface of lower jaw (242) includes an electrode surface (250) and a PTC body (254), similar to electrode surface (50) and PTC body (54) described above for jaw (42). PTC body (254) is disposed against exterior sides of electrode surface (250). Electrode surface (250) and PTC body (254) are both disposed above insulator body (340). Insulator (340) may comprise a plastic, such as GRIVORY plastic manufactured by EMS-Chemie (North America), Inc., or any other suitable insulating material as will be apparent to those of ordinary skill in the art in view of the teachings herein. Insulator (340) may also include grasping teeth or serrations on an exterior top portion of the insulator (340), to assist with grasping tissue between lower jaw (242) and upper jaw (244).

Stud-receiving member (300) may also comprise a GRIVORY plastic as made by EMS-Chemie (North America), Inc. or any other suitable insulator as will be apparent to those of ordinary skill in the art in view of the teachings herein. Stud-receiving member (300) may operate as a heat stake gasket or other suitable component as will be apparent to those of ordinary skill in the art in view of the teachings herein. During assembly of stud-receiving member (300) to insulator body (340), a shim or other suitable device may be disposed between jaws (242, 244) to set a desired gap. For instance, PTC body (254) and the electrode including electrode surface (250) may be joined to a shim that assists to form the appropriate gap between jaws (242, 244).

Figure 12:
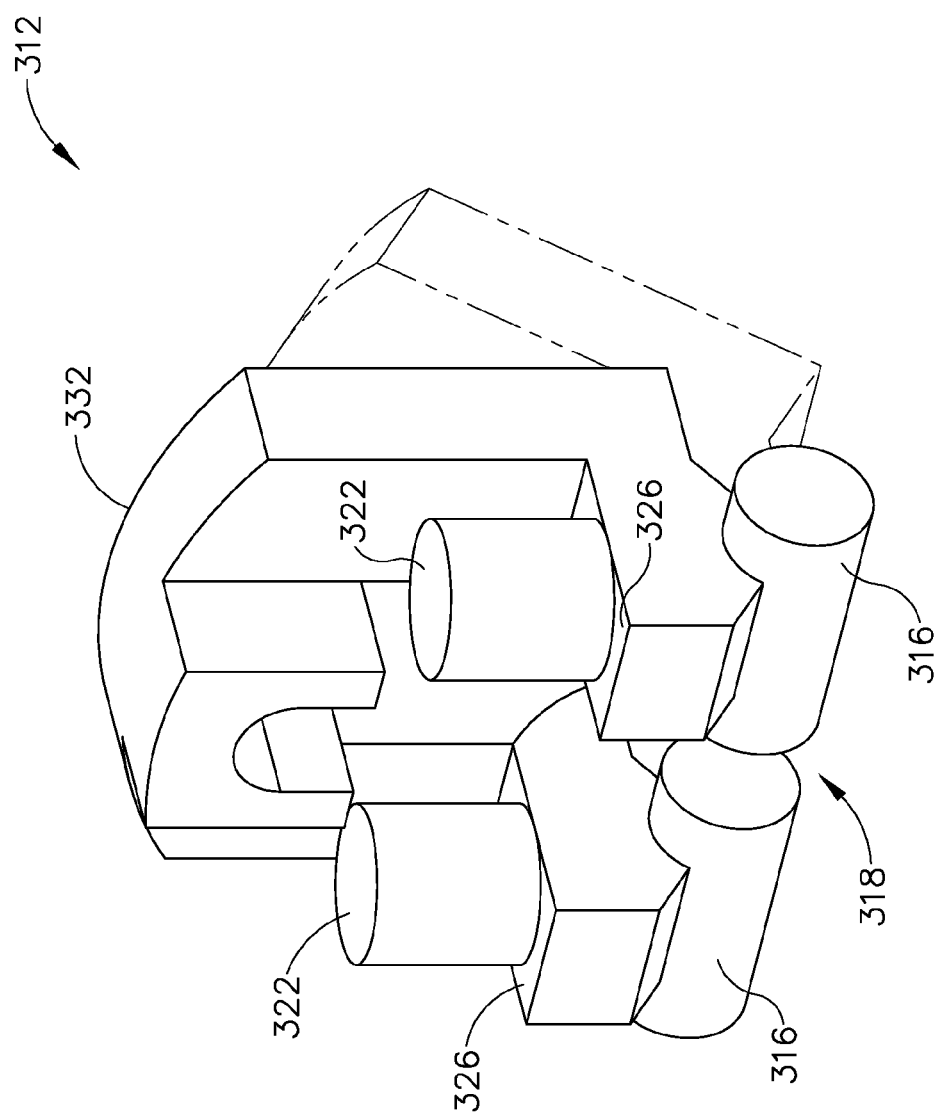
FIG. 12 depicts a perspective view of a pivoting jaw closure member of the end effector of FIG. 8.
Figure 13A:
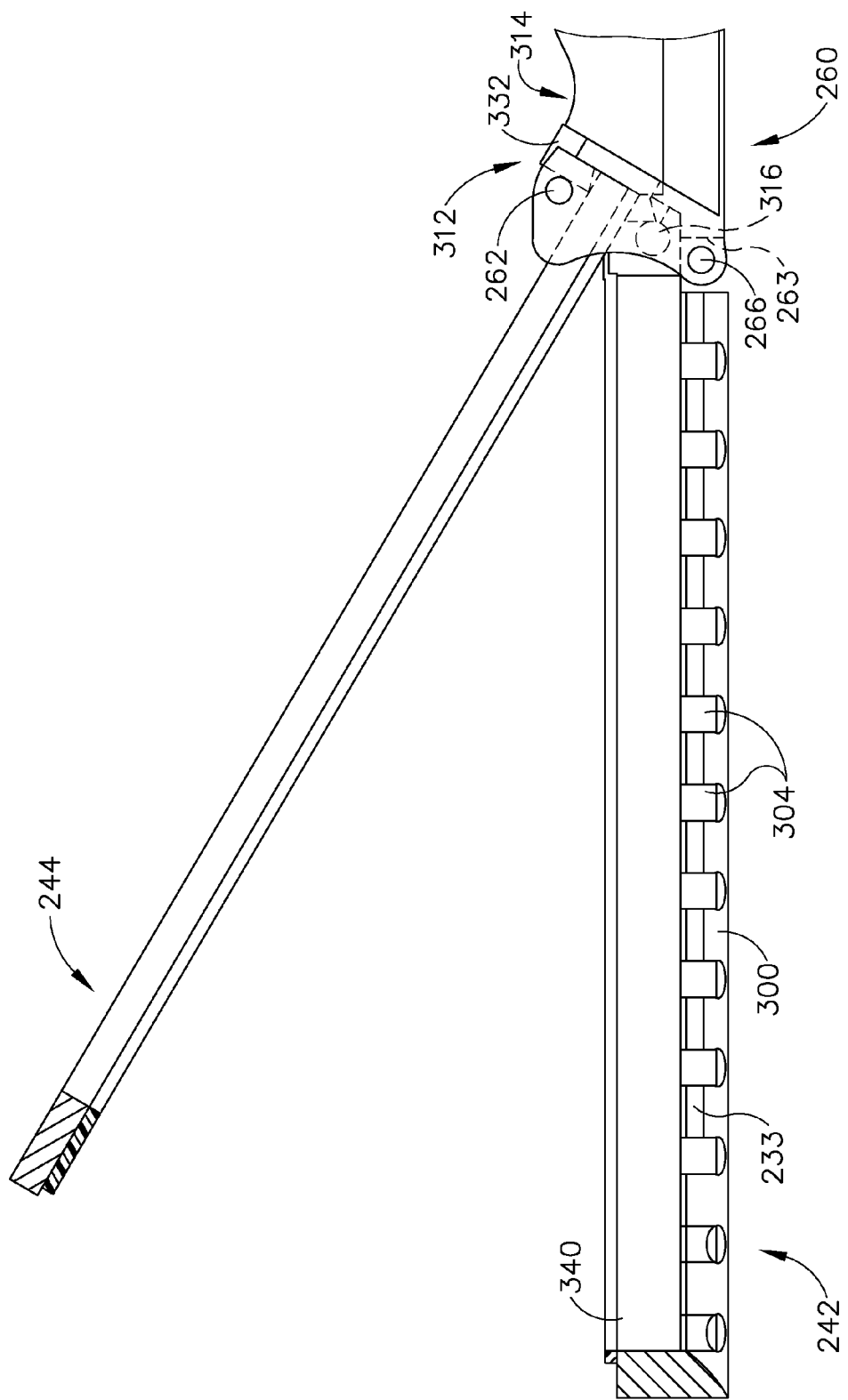
FIG. 13A depicts a partial, side elevational view of the end effector of FIG. 8 in which the upper jaw is in an open position with respect to the lower jaw.
Figure 13B:
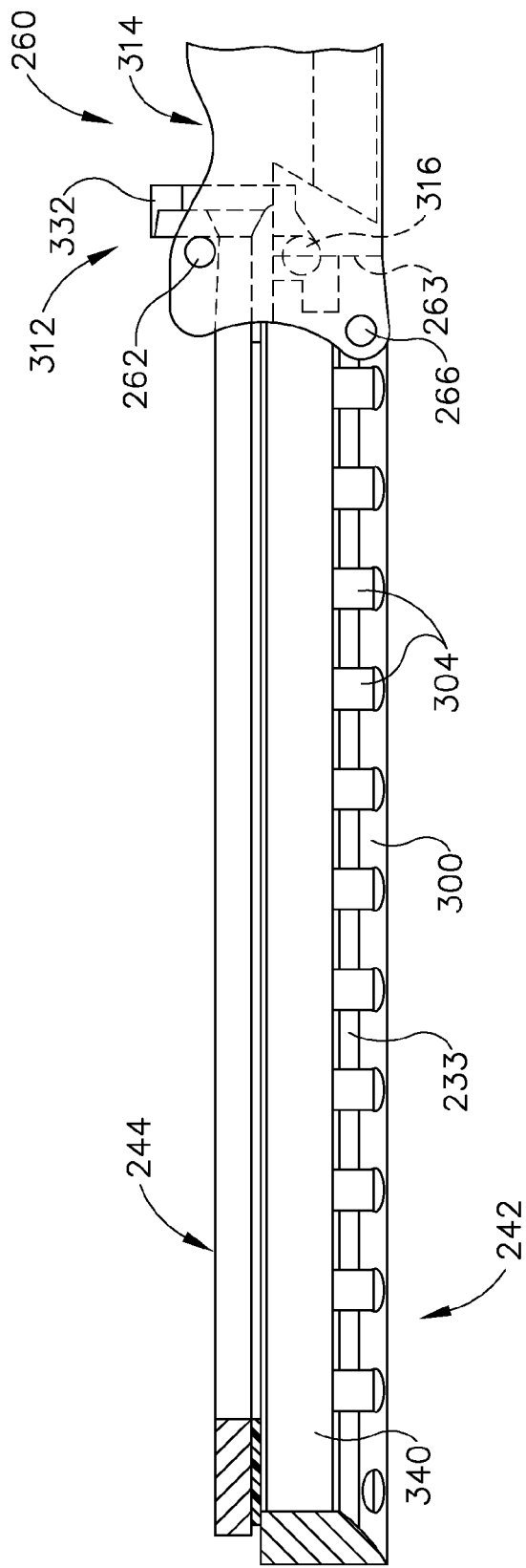
FIG. 13B depicts a partial, side elevational view of the end effector of FIG. 8 in which the upper jaw is in a closed position with respect to the lower jaw.

FIG. 12 shows a pivoting member (312), and FIGS. 13A-13B show how pivoting member (312) assists to transition upper jaw (244) between an open position (FIG. 13A) and a closed position (FIG. 13B) relative to lower jaw (242). Pivoting member (312) is a single piece of metal injection molded stainless steel in the present example, though it should be understood that any other suitable material(s) or construction may be used. Pivoting member (312) includes outwardly extending pivot pin features (316) that are separated by a slot (318), which is sized and shaped to receive a portion of firing beam (260). Pivot pin features (316) provide a pivotal coupling of pivoting member (312) with lower jaw (242). Pivoting member (312) further includes pins (322) that extend upwardly from shelves (326). Pins (322) are sized and shaped for receipt within notches (324) that are located at the proximal end of upper jaw (244). Notches (324) are best seen in FIG. 11. Shelves (326) and pins (322) together provide structural support for upper jaw (244) as upper jaw (244) transitions between open and closed positions. A proximal wall (332) of pivoting member (312) extends upwardly and is substantially perpendicular to shelves (326).

When firing beam (260) is in a proximal position as shown in FIG. 13A, upper pins (262) of firing beam (260) bear against proximal wall (332) to hold upper jaw (244) in the open position. As also shown in FIG. 13A, a wall (263) acts as a stop against lower pins (266) of firing beam, thereby restricting further proximal movement of firing beam (260). As firing beam (260) is advanced distally, pin (262) bears down against upper jaw (244) as described above to urge upper jaw (244) toward lower jaw (242). During this motion, pivoting member (312) pivots at pivot pin features (316) to the position shown in FIG. 13B. It should be noted that, in this example, jaws (242, 244) are fully closed before firing beam (260) advances distally far enough to sever tissue capture between jaws (242, 244). Thus, it is possible to grasp tissue between jaws (242, 244) and then release the tissue, without cutting the tissue. It is also possible to clamp and seal the tissue between jaws (242, 244) and then release the tissue, without cutting the tissue. Of course, firing beam (260) may be advanced further distally to cut tissue captured between jaws (242, 244). When firing beam (260) is retracted proximally, upper pins (262) again engage against proximal wall (332), eventually pivoting the pivoting member (312) at pivot pin features (316) to transition upper jaw (244) back to the open position.

In use, tissue is clamped between jaws (242, 244) as described above. Firing beam (260) is then advanced along upper jaw (244) to urge upper jaw (244) toward lower jaw (242) while clamping tissue and severing the clamped tissue. Firing beam (160) advances to a distal-most position in which upper jaw (242) is substantially parallel to lower jaw (142). Electrodes along the lengths of jaws (242, 244) of end effector may seal the edges surrounding the severed tissue in a manner as described above for end effector (40). For example, current may flow between PTC body (254) of lower jaw (242) and electrode surface (252) of upper jaw (244). Current may also flow between electrode surface (250) of lower jaw (242) and electrode surface (252) of upper jaw (244). Additionally or alternatively, current may flow between electrode surface (250) of lower jaw (242) and firing beam (260). Firing beam (260) may then be retracted to open jaws (242, 244), thereby releasing the tissue.

C. Exemplary Hinged Segmented Jaws

Figure 15:
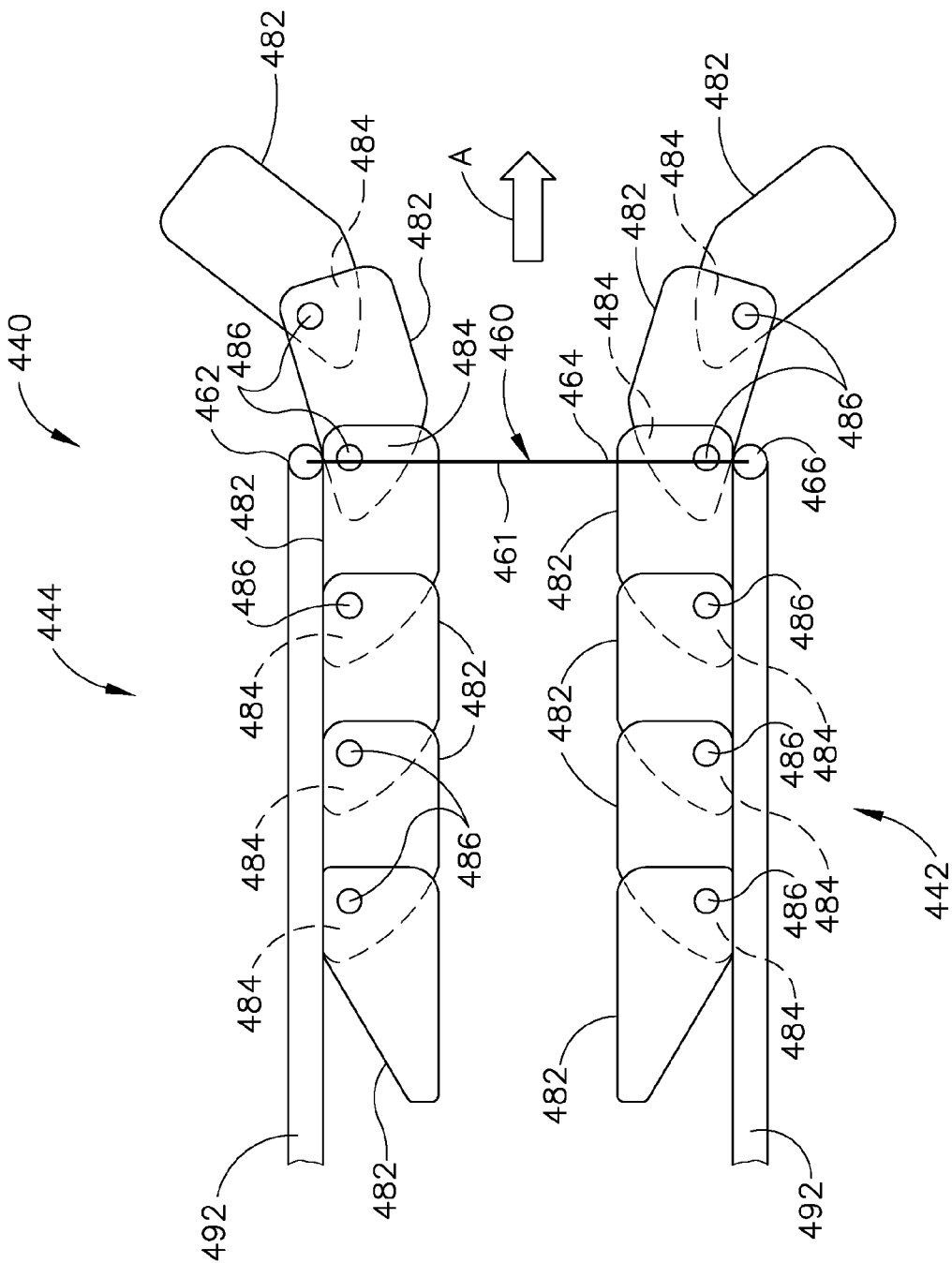
FIG. 15 depicts a side elevational view of an exemplary alternative end effector having jaws formed by hinged segments.

FIG. 15 shows another exemplary set of jaws (424, 444) of an end effector (440), which may also be used as a substitute for end effector (40). Both jaws (424, 444) have segments (482) adjoined at hinged portions (484) by pins (486). Segments (482) are pivotable with respect to one another at pins (486). Each hinged portion (484) includes a pair of lateral recesses that together define a proximally projecting tongue. Each tongue is disposed in a slot formed at the distal end of the adjacent segment (482). Each tongue is also tapered in this example. A pin (486) passes through each tongue to pivotally couple each segment (482) with the adjacent segment (482).

Firing beam (460) is similar to firing beam (160) in that firing beam (460) urges jaws (424, 444) together and severs tissue that is captured between jaws (424, 444). Firing beam (460) includes closure pins (462, 466) that drive along the outer surfaces of jaws (424, 444). Thus, as firing beam (460) is advanced distally in the direction of arrow (A), segments (482) of jaws (424, 444) are urged toward each other to eventually align with each other in a substantially parallel arrangement. Distal closure pins (462, 466) may comprise rollers or other suitable features as will be apparent to those of ordinary skill in the art in view of the teachings herein. It should be understood that any firing beam referred to herein may include rollers as well. Hinged portions (484) may allow segments (482) to hinge slightly beyond an aligned, parallel position to increase tolerance associated with segments (482) and to minimize a force required to drive firing beam (460) distally. Firing beam (460) also includes a proximal resilient tail member (492) that assists to keep segments (482) aligned to ease the return stroke of firing beam (460). Tail member (492) may comprise a channel that is formed in firing beam (460) and that receives the outer edges of each segment (482).

It should be understood that distal advancement of firing beam (460) creates a progressive compression across segments (482) of jaws (442, 444) in which the greatest amount of compression is at the location of distal closure pins (162, 166) of the firing beam (460). Portions of jaws (442, 444) distal to the location of distal closure pins (162, 166) may still be compressing against clamped tissue, but with less force than the force imposed by parallel portions of jaws (442, 444) against the clamped tissue. Thus, a force required to advance firing beam (460) to clamp segmented jaws (442, 444) against tissue may be less than the force that would be required if rigid, non-segmented jaws were used. With the compression force being progressively and discretely applied to segments (482) with the advancement of firing beam (460), jaws (424, 444) may have a greater tolerance for stresses encountered from thick or dense tissues than might otherwise be tolerated by rigid, non-segmented jaws.

A cutting feature (461) extends between closure pins (462, 466). Cutting feature (461) is operable to sever tissue clamped between jaws (424, 444) as firing beam (460) advances through the tissue. In some versions, cutting feature (461) comprises a wire. In some other versions, cutting feature (461) comprises a blade. Other suitable forms that cutting feature (461) may take will be apparent to those of ordinary skill in the art in view of the teachings herein.

In use, when jaws (442, 444) clamp down across tissue as described above and firing beam (460) advanced, the clamped tissue is severed by cutting feature (461) of firing beam (460). Electrodes across mutually-facing interior surfaces of jaws (442, 444) are operable to seal the severed tissue. In some versions, the electrodes are formed by conductive segments that are separately disposed on segments (482) and that establish continuity once adjacent segments are substantially parallel or aligned with each other. In some other versions, the electrodes are formed by flexible wires that extend along the mutually-facing interior surfaces of jaws (442, 444). As yet another merely illustrative example, the electrodes may be formed by flexible conductive bands or strips that extend along the mutually-facing interior surfaces of jaws (442, 444). Other suitable ways in which electrodes may be incorporated into jaws (442, 444) will be apparent to those of ordinary skill in the art in view of the teachings herein.

In the present example, pins (486) are disposed near the outer regions of jaws (442, 444). In particular, pins (486) of upper jaw (444) are positioned near the upper region of upper jaw (444); while pins (486) of lower jaw (442) are positioned near the lower region of lower jaw (442). Thus, upper jaw (444) pivots at points positioned near the upper region of upper jaw (444); while lower jaw (442) pivots at points positioned near the lower region of lower jaw (442). In some other versions, pins (486) of upper jaw (444) are positioned near the lower region of upper jaw (444); while pins (486) of lower jaw (442) are positioned near the upper region of lower jaw (442). In such versions, upper jaw (444) would pivot at points positioned near the lower region of upper jaw (444); while lower jaw (442) would pivot at points positioned near the upper region of lower jaw (442). Such a configuration may make it easier to apply wire/band/strip types of electrodes across segments (482) of each jaw (442, 444), as such types of electrodes would not have to longitudinally stretch or flex as much when jaws (442, 444) are pivotally splayed apart to a significant degree.

As yet another merely illustrative variation, end effector (440) may comprise one jaw (442, 444) that is formed by pivoting segments (482) and another jaw (442, 444) that is rigid and non-segmented (e.g., like a conventional jaw, etc.). In some such versions, the rigid, non-segmented jaw (442, 444) has one or more electrode surfaces while the flexible jaw (442, 444) lacks electrode surfaces. Of course, firing beam (460) may have one or more electrode surfaces in such versions. Other suitable variations of end effector (440) will be apparent to those of ordinary skill in the art in view of the teachings herein.

D. Exemplary Sliding Segmented Jaws

Figure 16:
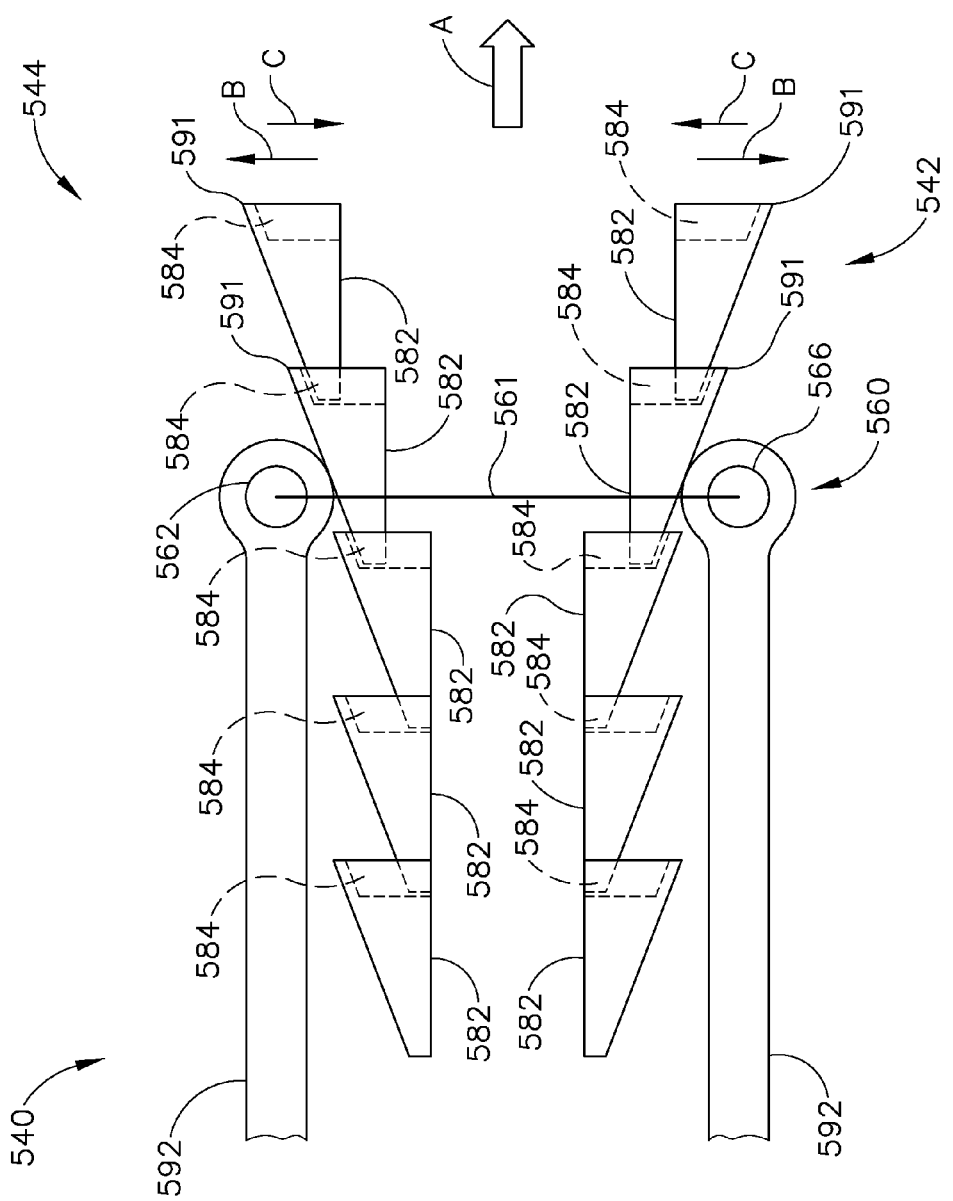
FIG. 16 depicts a side elevational view of another exemplary alternative end effector having jaws formed by sliding segments.

FIG. 16 shows jaws (524, 544) of end effector (540), which may also be used as a substitute for end effector (40). Both jaws (524, 544) have segments (582) adjoined via sliding portions (584). A sliding portion (484) of a first segment (582) defines a recess that receives and has a greater height than a tapered proximal portion of a second segment (582). The second segment (582) may be attached to sliding portion (584) of the first segment (582) via a pin or other feature that extends from the tapered proximal portion of the second segment (582) and that is slidably received in a slot defined in sliding portion (484) of the first segment (582). Other suitable manners of attachment will be apparent to those of ordinary skill in the art in view of the teachings herein. For instance, the distal slot and the proximal end of each segment (582) may have a complementary dovetail configuration. Segments (582) are able to slide to the directions of arrows (B, C) when received in sliding portions (584). In some versions, segments (582) include resilient members configured to bias segments (582) of jaw (544) in the direction of arrow (B) and segments (582) of jaw (542) in the direction of arrow (C) prior to the advancement of distal pins (562, 566) to urge jaws (542, 544) together.

Firing beam (560) is similar to firing beam (160) described above. As firing beam (560) advances distally in the direction of arrow (A), distal closure pins (562, 566) urge segments (582) of jaw (544) to move in the direction of arrow (C) and segments (582) of jaw (542) to move in the direction of arrow (B) until segments (582) of jaw (544) are aligned with each other and segments (582) of jaw (542) are aligned with each other. At such a stage, segments (582) of jaw (544) together form a tissue contacting surface that is generally parallel with an opposing tissue contacting surface formed by segments (582) of jaw (542). Distal closure pins (562, 566) may comprise rollers or other suitable features as will be apparent to those of ordinary skill in the art in view of the teachings herein. Firing beam (560) also includes a proximal tail member (592) that assists to keep segments (582) aligned to ease the return stroke of firing beam (560). Tail member (592) may comprise a channel that is formed in firing beam (560) and that receives the outer tips (591) of each segment (582).

Thus, distal advancement of firing beam (560) creates a progressive compression across segments (582) of jaws (542, 544) in which the greatest amount of compression is at the location of distal closure pins (562, 566) of the firing beam (560). Portions of jaws (542, 544) distal to the location of distal closure pins (562, 566) may still be compressing against clamped tissue, but with less force than the force imposed by proximal portions of jaws (542, 544) against the clamped tissue. Thus, a force required to advance firing beam (560) to clamp segmented jaws (542, 544) against tissue may be less than the force that would be required if rigid, non-segmented jaws were used. Jaws (542, 544) in a fully closed position may remain parallel, with respective sets of segments (582) aligned, to ease the return stroke of firing beam (560).

A cutting feature (561) extends between closure pins (562, 566). Cutting feature (561) is operable to sever tissue clamped between jaws (524, 544) as firing beam (560) advances through the tissue. In some versions, cutting feature (561) comprises a wire. In some other versions, cutting feature (561) comprises a blade. Other suitable forms that cutting feature (561) may take will be apparent to those of ordinary skill in the art in view of the teachings herein. In use, when jaws (542, 544) clamp down across tissue as described above and firing beam (560) advanced, the clamped tissue is severed by cutting feature of firing beam (560).

Figure 17:
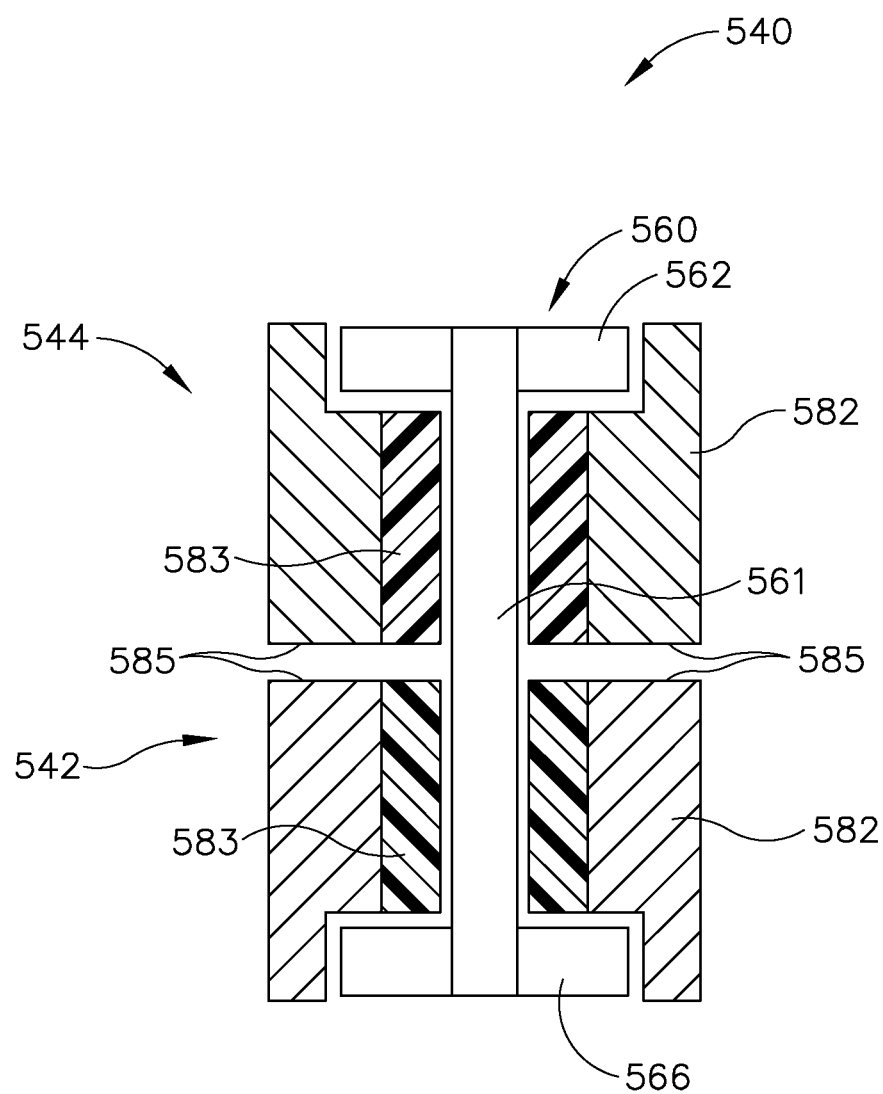
FIG. 17 depicts a front cross-sectional view of the end effector of FIG. 16.

Electrodes across mutually-facing interior surfaces of jaws (542, 544) are operable to seal the severed tissue. In the present example, segments (582) are formed of a conductive material such as any suitable metal. As shown in FIG. 17, each segment (582) also includes a non-conductive portion (583) adjacent to firing beam (560). In some versions, non-conductive portion (583) comprises a plastic insert. In some other versions, non-conductive portion (583) comprises an insulative coating. Other suitable forms that non-nonductive portion may take will be apparent to those of ordinary skill in the art in view of the teachings herein. Non-conductive portions (583) are configured to leave conductive tissue-contacting surfaces (585) exposed, such that surfaces (585) directly contact tissue that is clamped between jaws (542, 544). Surfaces (585) may thus act as the electrodes and may thus be used to deliver bipolar energy to tissue clamped between jaws (542, 544). In some versions, surfaces (585) of jaw (542) provide a first polarity while surfaces (585) of jaw (544) provide a second polarity. As another merely illustrative variation, cutting feature (561) may provide a first polarity while surfaces (585) of both jaws (542, 544) provide a second polarity. In such versions, insulative material may be used to prevent any short circuits between cutting feature (561) and jaws (542, 544) via closure pins (562, 566). As yet another merely illustrative variation, surfaces (585) may be substituted with conductive segments that are separately disposed on segments (582) and that establish continuity once adjacent segments are substantially parallel or aligned with each other; with flexible wires that extend along the mutually-facing interior surfaces of jaws (542, 544); or with flexible conductive bands or strips that extend along the mutually-facing interior surfaces of jaws (542, 544). Other suitable arrangements will be apparent to those of ordinary skill in the art in view of the teachings herein.

As yet another merely illustrative variation, end effector (540) may comprise one jaw (542, 544) that is formed by sliding segments (582) and another jaw (542, 544) that is rigid and non-segmented (e.g., like a conventional jaw, etc.). In some such versions, the rigid, non-segmented jaw (542, 544) has one or more electrode surfaces while the flexible jaw (542, 544) lacks electrode surfaces. Of course, firing beam (560) may have one or more electrode surfaces in such versions. Other suitable variations of end effector (540) will be apparent to those of ordinary skill in the art in view of the teachings herein.

E. Exemplary Segmented Knife

Figure 18:
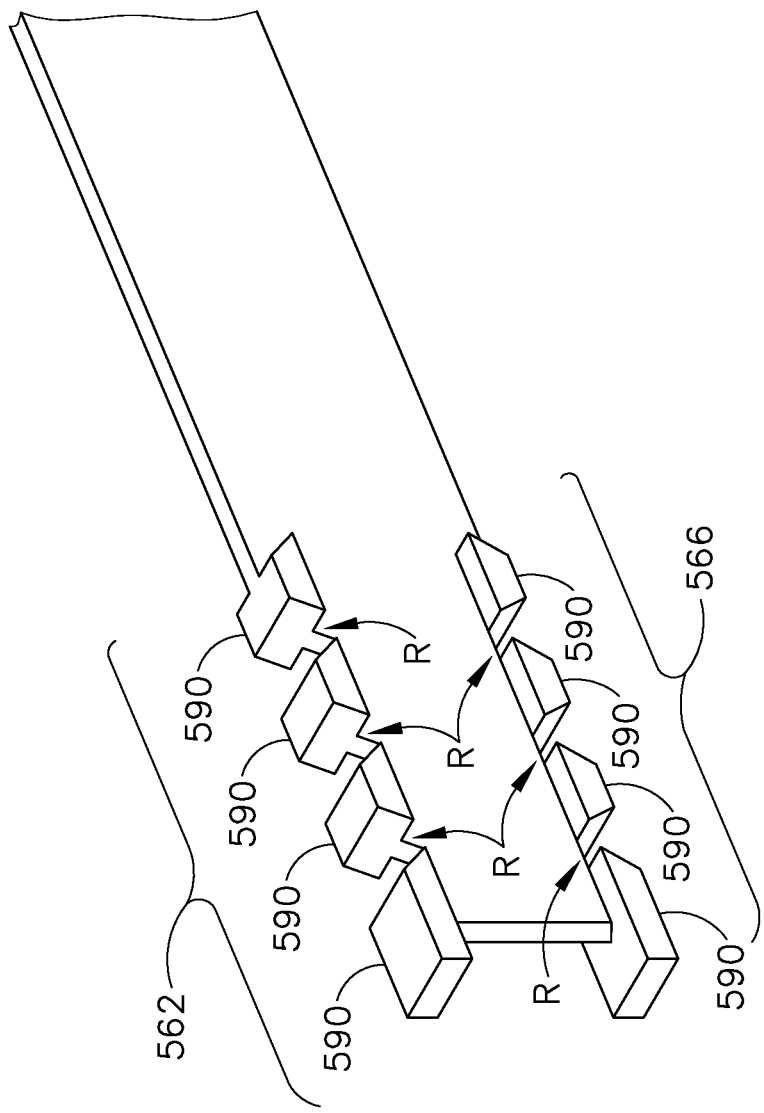
FIG. 18 depicts a perspective view of an exemplary alternative firing beam that includes segmented upper and lower flanges.

FIG. 18 shows exemplary knife or firing beam (660). Any firing beam of the present disclosure may be modified with the features of firing beam (660) described below and vice versa. Firing beam (660) includes flanged portions (562, 566) that operate in a similar manner to flanges (62, 66) described above for firing beam (60). Flanged portions (562, 566) include segments (590) separated by recess portions (R) and that provide interruptions within flanged portions (562, 566). Segments (590) allow firing beam (660) to more easily flex around a slot defined in a curved jaw, as described above. Further, the interruptions provided by segments (590) increase the load carrying capabilities for firing beam (560) that may otherwise crack under abusive tissue loads. Thus, firing beam (560) may compress thicker clamped tissue portions than a firing beam that may lack segments (590). Other suitable firing beam variations will be apparent to those of ordinary skill in the art in view of the teachings herein.

Figure 19:
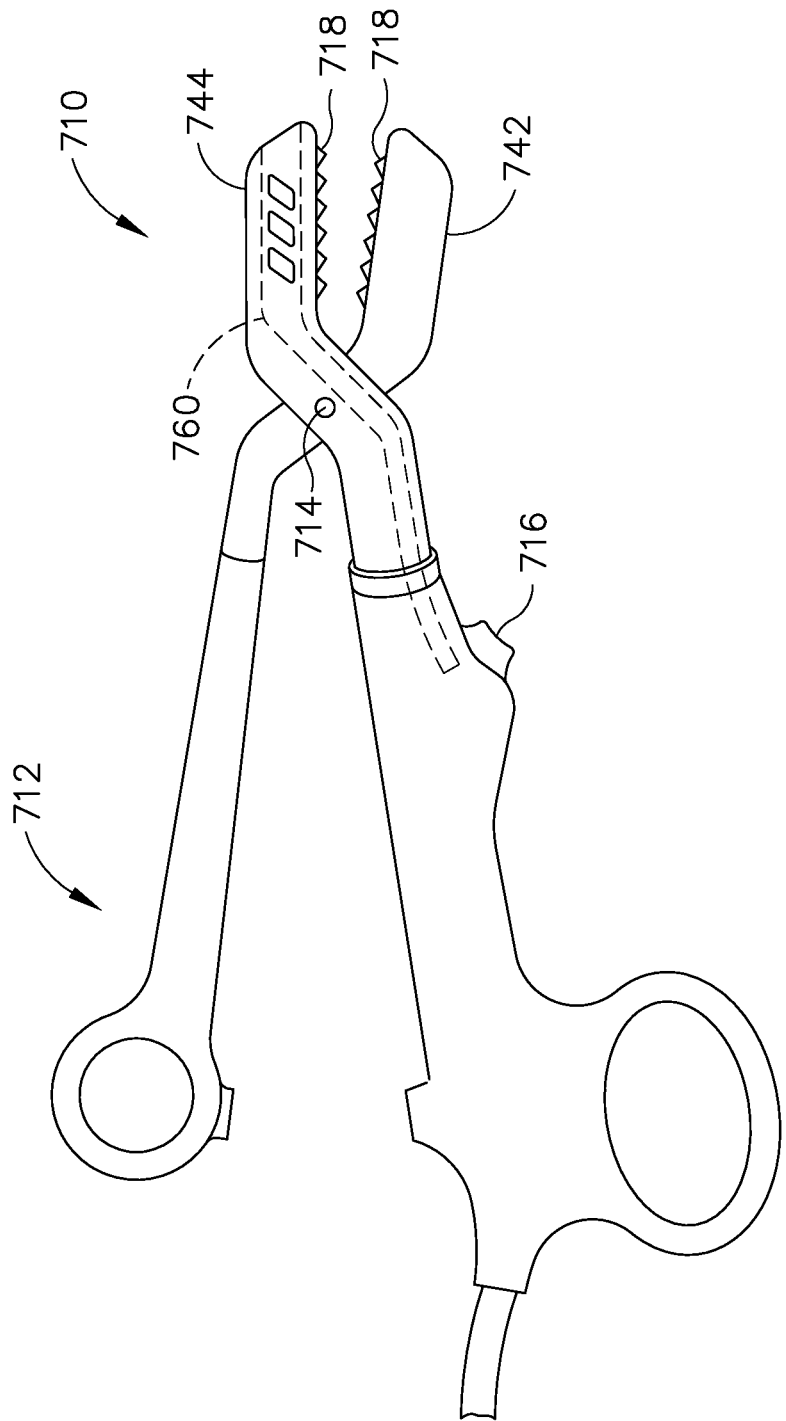
FIG. 19 depicts a side elevational view of an exemplary electrosurgical forceps assembly.

III. Exemplary Electrosurgical Forceps Assembly with Modular Electrode Cartridge FIG. 19 shows an exemplary forceps assembly (710), which is usable as an alternative to instrument (10), though it should be understood that forceps assembly (710) and the teachings below may be readily modified for incorporation into instrument (10) in a manner as will be apparent to those of ordinary skill in the art in view of the teachings herein. Forceps assembly (710) has a scissor grip (712), clamping jaws (742, 744), and a knife blade (760). Jaws (742, 744) pivot about a pivot point (714). Jaws (742, 744) include serrations such as grasping teeth (718) to assist with grasping tissue clamped between jaws (742, 744). A knife blade (760) is positioned in upper jaw (744) and may be driven toward a surface of lower jaw (742), to sever tissue captured between jaws (742, 744). Trigger (716) actuates knife blade (760) in a manner as will be apparent to one of ordinary skill in the art in view of the teachings herein. In some other versions, knife blade (760) is omitted.

Figure 20:
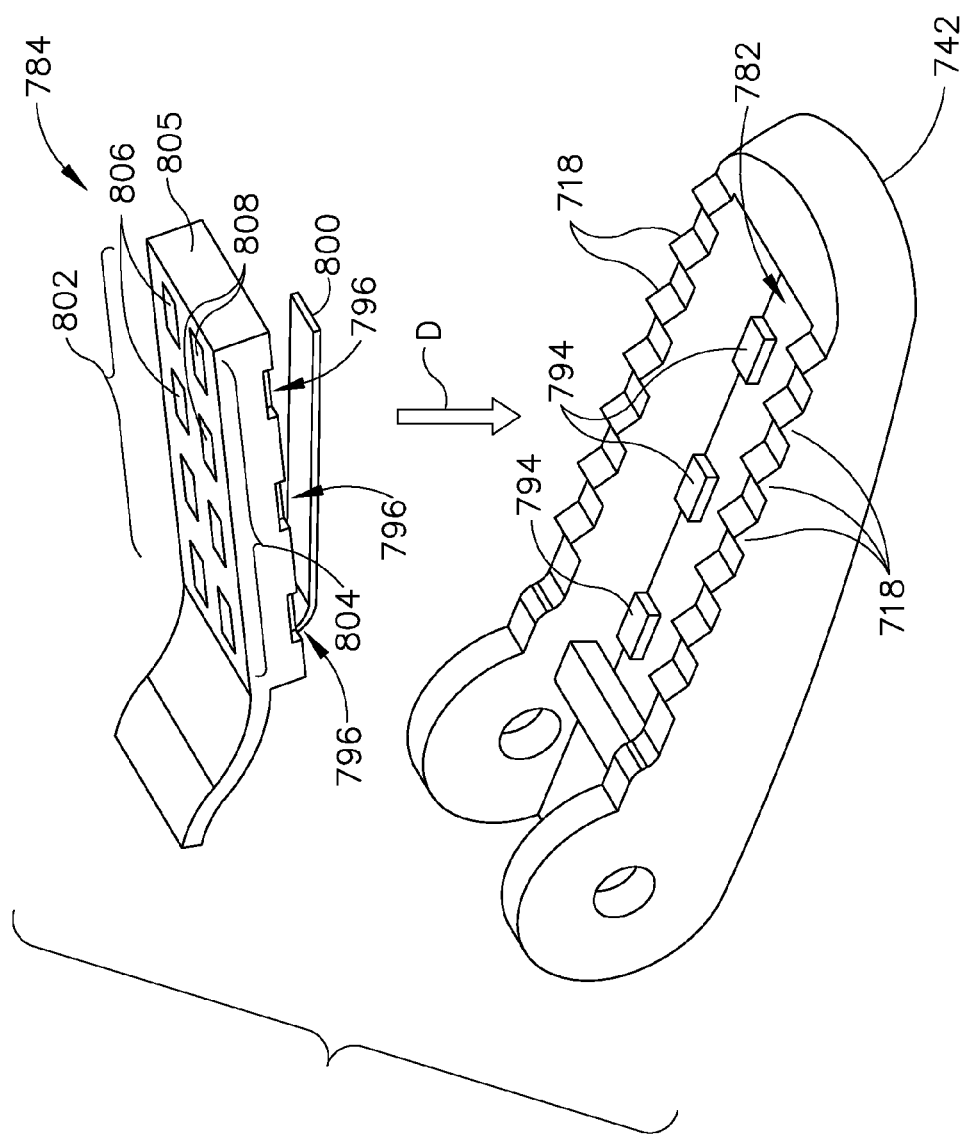
FIG. 20 depicts an exploded fragmentary view of an exemplary electrode cartridge configured for placement within a lower jaw of the assembly of FIG. 19.
Figure 21:
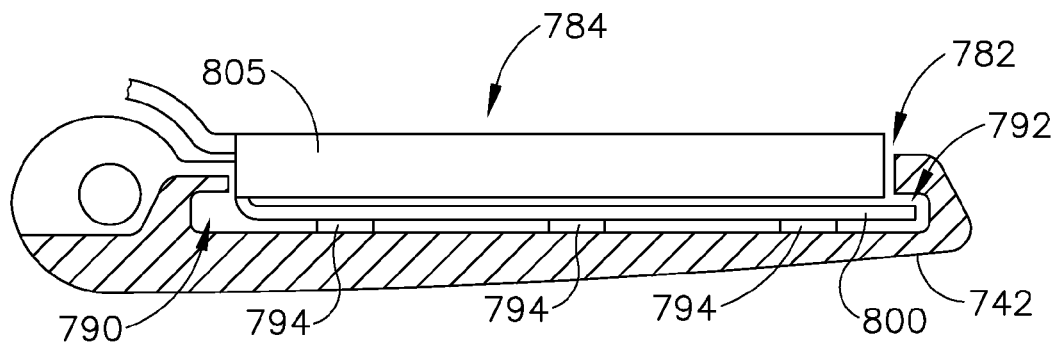
FIG. 21 depicts a side elevational view of the electrode cartridge of FIG. 20 disposed in the lower jaw of the assembly of FIG. 19.
Figure 22:
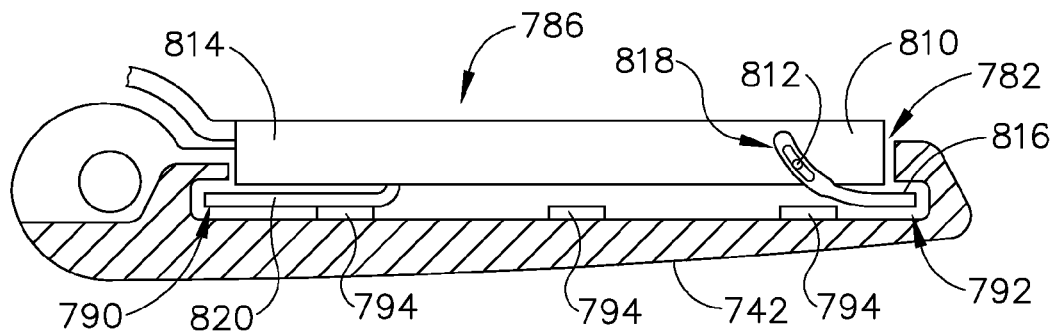
FIG. 22 depicts a side elevational view of an alternative electrode cartridge disposed in the lower jaw of the assembly of FIG. 19.
Figure 23:
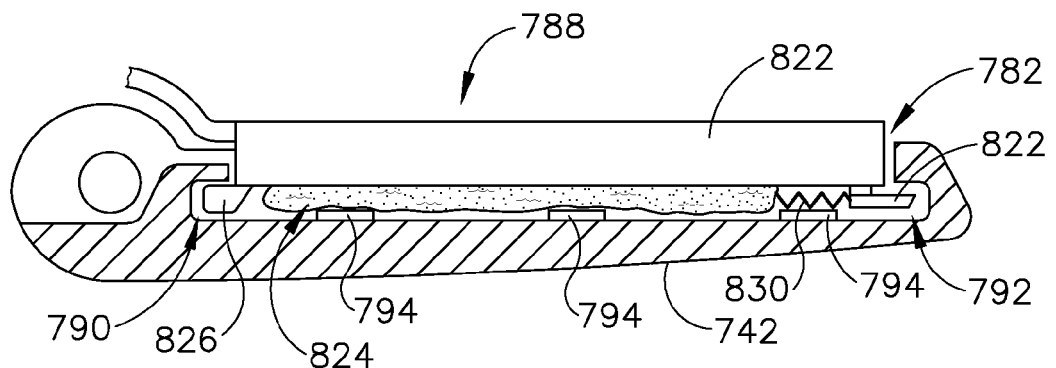
FIG. 23 depicts a side elevational view of another alternative electrode cartridge disposed in the lower jaw of the assembly of FIG. 19.

FIG. 20 shows a recess (782) defined in lower jaw (742). Recess (782) is sized and shaped to receive a modular electrode cartridge such as cartridges (784, 786, 788) respectively shown in FIGS. 21-23. As shown in FIGS. 21-23 recess (782) includes a proximal notch (790) and a distal notch (792). Lower jaw (742) also includes cartridge receiving bosses (794) that are sized and shaped to engage notches (796) disposed on side surfaces of cartridge (784). In some versions, bosses (794) are configured to provide an interference fit between cartridge (784, 786, 788) and lower jaw (742) when cartridge (784, 786, 788) is fully received in lower jaw (742) and is disposed below teeth (718) of lower jaw (742). In addition or the alternative, bosses (794) may serve as spacers to prevent the underside of cartridges (784, 786, 788) from contacting the lower surface cof recess (782).

FIG. 20 shows that bio-polar cartridge (784) includes a first electrode (802), a second electrode (804), and a cantilevered arm spring (800) disposed below body (805). Surfaces (806, 808) of electrodes (802, 804) are exposed through openings defined in an upper surface of cartridge (784). While a single cartridge (784) includes both electrodes (802, 804) in this example, other examples may include two separate electrode cartridges, with each cartridge including a single electrode, etc. The longitudinally extending surface located between first electrode (802) and second electrode (804) presents a cutting board for knife blade (760) to sever tissue clamped between jaws (742, 744).

Cartridge (784) may be dropped in the direction of arrow (D) for receipt within recess (782) of lower jaw (742). Cantilever spring arm (800) includes a distal end that is received in distal notch (792), as best seen in FIG. 21. Cantilevered spring arm (800) biases cartridge (784) upwardly from recess (782) such that an upper surface of cartridge (784) is resiliently positioned above teeth (718) of lower jaw (742). In such a floating position, and as electrodes (802, 804) are above and interior of teeth (718), tissue may be selectively coagulated via electrodes (802, 804) without grasping or clamping the tissue between teeth (718) of jaws (742, 744). Clamping of jaws (742, 744) against tissue controls the position of modular cartridge (784) within recess (782) of lower jaw (742) as the clamped tissue compresses downwardly in the direction of arrow (D) against cartridge (784). The use of a "floating" cartridge (784) may facilitate thermal isolation and heat dissipation via electrodes (802, 804) on the clamped tissue.

Cartridges (786, 788) function in a manner similar to cartridge (784) with some structural variations. FIG. 22 shows cartridge (786) as having a body (810), which has a pin (812) projecting from side surface (814). A cantilevered spring arm (816) includes an elongate slot (818) at a proximal end. Pin (812) is received within slot (818), which enables cantilevered spring arm (816) to slide relative to pin (812). Another cantilevered spring arm (820) extends proximally from body (810) for receipt within proximal notch (790). Cantilevered spring arms (816, 820) together bias cartridge (786) upwardly from recess (782) when cartridge (786) is received in recess (782), such that an upper surface of cartridge (786) is resiliently positioned above teeth (718) of lower jaw (742). Thus, tissue may be coagulated using cartridge (786) without grasping or clamping the tissue between teeth (718) of jaws (742, 744).

FIG. 23 shows cartridge (788), which has a body (822) and a bladder (824) projecting from an undersurface of body (822). Bladder (824) is insulative and is filled with a suitable liquid as will be apparent to those of ordinary skill in the art in view of the teachings herein. Cartridge (788) includes a proximal protrusion (826) and a distal protrusion (828). Proximal protrusion (826) is received within proximal notch (790) of lower jaw (742), and distal protrusion (828) is received within distal notch (792) of lower jaw (742). In particular, a spring (830) biases protrusion (828) distally into distal notch (792) to cooperate with proximal protrusion (826) for retaining cartridge (788) in lower jaw (742). Bladder (824) biases cartridge (788) upwardly from recess (782) when cartridge (788) is received in recess (782), such that an upper surface of cartridge (784) is resiliently positioned above teeth (718) of lower jaw (742). Thus, tissue may be coagulated using cartridge (786) without grasping or clamping the tissue between teeth (718) of jaws (742, 744).

IV. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) an end effector assembly comprising:
      (i) a first jaw, wherein the first jaw defines a slot, wherein the first jaw further comprises a plurality of segments extending along a first plane,
      (ii) a second jaw pivotally connected to the first jaw at a pivot point between an open position and a closed position, wherein the second jaw defines a slot corresponding with the slot of the first jaw, wherein the second jaw is configured to extend along a second plane that is parallel to the first plane when the second jaw is in the closed position, wherein the segments are moveable relative to each other away from the second plane to reach the open position, and
      (iii) a firing beam configured to be received within the slots defined by the first and second jaws, wherein the firing beam is operable to advance distally through the slots to close the jaws;
   (b) a body operable to communicate with the end effector assembly; and
   (c) a shaft extending from the body to the end effector assembly.

2. The apparatus of claim 1, wherein the first and second jaws comprise electrodes configured to seal tissue.

3. The apparatus of claim 1, wherein the first jaw further comprises living hinges joining the segments together.

4. The apparatus of claim 1, wherein the plurality of segments include a first segment and a second segment, wherein the first segment is movable between a first position in which the first segment is obliquely angled relative to the second segment and a second position in which the first segment is parallel to the second segment.

5. The apparatus of claim 1, wherein the firing beam includes closure pins operable to drive the first jaw toward the second jaw in response to distal advancement of the firing beam through the slots.

6. The apparatus of claim 5, wherein the closure pins are operable to discretely and directly drive each segment in a succession during distal advancement of the firing beam through the slots.

7. The apparatus of claim 5, wherein at least one of the first jaw or second jaw comprises a bearing surface configured to bear against the closure pins as the firing beam moves relative to the jaws, wherein the bearing surface comprises spring steel.

8. The apparatus of claim 7, wherein the bearing surface is electroplated.

9. The apparatus of claim 1, wherein the first jaw is compliant at interfaces between the segments, wherein the second jaw is rigid.

10. The apparatus of claim 1, wherein the segments are joined together by pivoting hinges.

11. The apparatus of claim 1, wherein the first jaw further comprises spaces between adjacent segments.

12. The apparatus of claim 1, wherein the firing beam comprises a distal cutting edge configured to sever tissue clamped between the first and second jaws.

13. The apparatus of claim 1, wherein the jaws include a curved configuration.

14. The apparatus of claim 1, wherein the first plane passes through the pivot point.

15. The apparatus of claim 1, wherein the first jaw is pivotable about the pivot point to move relative to the second jaw.

16. An apparatus for operating on tissue, the apparatus comprising:
   (a) an end effector assembly comprising:
      (i) a first jaw, wherein the first jaw defines a slot, wherein the first jaw further comprises a plurality of segments, wherein the segments are movable relative to one another,
      (ii) a second jaw pivotally connected to the first jaw at a pivot point, wherein the second jaw defines a slot corresponding with the slot of the first jaw, wherein the segments are configured to transition between:
         (A) a first configuration where less than all of the segments are parallel with the second jaw such that less than all of the segments are in a closed position relative to the second jaw, and
         (B) a second configuration where all of the segments are parallel with the second jaw such that all of the segments are in a closed position relative to the second jaw,
      (iii) a firing beam configured to be received within the slots defined by the first and second jaws, wherein the firing beam is operable to advance distally through the slots to progressively close one or more of the segments relative to the second jaw;
   (b) a body operable to communicate with the end effector assembly; and
   (c) a shaft extending from the body to the end effector assembly.

17. The apparatus of claim 16, wherein when the segments are in the first configuration, at least one of the segments is in the closed position relative to the second jaw and at least another of the segments is in the open position relative to the second jaw.

18. The apparatus of claim 16, wherein the first jaw is pivotable about the pivot point to move in a first direction towards the second jaw and in a second direction away from the second jaw, wherein the segments are movable relative to one another in the second direction.

19. The apparatus of claim 16, wherein the first jaw further comprises living hinges joining the segments together.

20. An apparatus for operating on tissue, the apparatus comprising:
   (a) an end effector assembly comprising:
      (i) a first jaw, wherein the first jaw defines a slot, wherein the first jaw further comprises a plurality of segments,
      (ii) a second jaw pivotally connected to the first jaw at a pivot point, wherein the second jaw defines a slot corresponding with the slot of the first jaw, wherein the first jaw is pivotable about the pivot point to move in a first direction towards the second jaw and in a second direction away from the second jaw, wherein the segments are movable relative to one another in the second direction, (iii) a firing beam configured to be received within the slots defined by the first and second jaws, wherein the firing beam is operable to advance distally through the slot to close the jaws;

(b) a body operable to communicate with the end effector assembly; and (c) a shaft extending from the body to the end effector assembly.

* * * * *